US009370617B2

(12) United States Patent
Chepurny

(10) Patent No.: US 9,370,617 B2
(45) Date of Patent: Jun. 21, 2016

(54) CARRIER FOR PATIENT FLUIDS

(75) Inventor: Mark P. Chepurny, Bradford (CA)

(73) Assignee: Notion Medical Inc., Toronto, Ontario (CA)

( * ) Notice: Subject to any disclaimer, the term of this patent is extended or adjusted under 35 U.S.C. 154(b) by 0 days.

(21) Appl. No.: 13/882,881

(22) PCT Filed: Oct. 27, 2011

(86) PCT No.: PCT/CA2011/001196
§ 371 (c)(1),
(2), (4) Date: Jul. 22, 2013

(87) PCT Pub. No.: WO2012/058750
PCT Pub. Date: May 10, 2012

(65) Prior Publication Data
US 2013/0292521 A1    Nov. 7, 2013

(30) Foreign Application Priority Data

Nov. 1, 2010    (CA) ..................................... 2719687

(51) Int. Cl.
*F16M 11/10*   (2006.01)
*A61M 5/14*    (2006.01)
*A61G 12/00*   (2006.01)

(52) U.S. Cl.
CPC ............ *A61M 5/1415* (2013.01); *A61G 12/008* (2013.01)

(58) Field of Classification Search
CPC .......... A61M 5/1415; A61M 5/16818; A61M 5/1417; A61M 3/0266; A61M 5/1414; A61G 7/0503; A61G 12/008
USPC ....................................................... 248/125.3
See application file for complete search history.

(56) References Cited

U.S. PATENT DOCUMENTS

| | | | |
|---|---|---|---|
| 365,748 A * | 6/1887 | Jacoby | ............................ 248/94 |
| 417,997 A | 12/1889 | Dupuis | |
| 589,806 A | 9/1897 | Bard | |
| 730,358 A | 6/1903 | Fladby | |
| 2,983,474 A | 5/1961 | Hanna | |
| 4,332,378 A | 6/1982 | Pryor | |
| 4,511,158 A | 4/1985 | Varga et al. | |
| 4,572,536 A | 2/1986 | Doughty | |
| 4,729,576 A | 3/1988 | Roach | |
| 4,886,237 A | 12/1989 | Dennis | |
| 4,969,768 A | 11/1990 | Young | |
| 5,110,076 A | 5/1992 | Snyder et al. | |

(Continued)

FOREIGN PATENT DOCUMENTS

| | | |
|---|---|---|
| AU | 2003100759 A4 | 1/2004 |
| AU | 2005100583 A4 | 8/2005 |

(Continued)

*Primary Examiner* — Bradley Duckworth
(74) *Attorney, Agent, or Firm* — The Webb Law Firm

(57) ABSTRACT

A carrier for carrying patient fluids comprising a carrying frame, a support base, at least one container holder, attached to the carrying frame distal from the floor, configured to receive a container of medication, the container holder being movable between an upward position and a downward position, a holder activator spaced from the container holder and positioned between the container holder and the floor, coupled to the container holder, and configured such that the container holder moves toward a downward position in response to a first movement of the holder activator, and toward an upward position in response to a second movement of the holder activator.

15 Claims, 21 Drawing Sheets

(56) References Cited

U.S. PATENT DOCUMENTS

| | | |
|---|---|---|
| 5,112,019 A | 5/1992 | Metzler et al. |
| 5,188,323 A | 2/1993 | David |
| 5,219,139 A | 6/1993 | Hertzler et al. |
| 5,236,213 A | 8/1993 | Trickett |
| 5,288,093 A | 2/1994 | Gross |
| 5,337,992 A | 8/1994 | Pryor et al. |
| 5,374,074 A | 12/1994 | Smith |
| 5,509,680 A | 4/1996 | Scharf et al. |
| 5,728,077 A | 3/1998 | Williams et al. |
| 5,820,086 A | 10/1998 | Hoftman et al. |
| 6,036,147 A * | 3/2000 | Militzer ............... 248/159 |
| 6,079,678 A | 6/2000 | Schott et al. |
| 6,179,260 B1 | 1/2001 | Ohanian |
| 6,409,131 B1 | 6/2002 | Bentley et al. |
| 6,966,086 B2 * | 11/2005 | Metz et al. ............... 5/510 |
| 7,624,953 B2 | 12/2009 | Silverman et al. |
| 7,637,464 B2 | 12/2009 | Heimbrock et al. |
| 7,731,136 B1 | 6/2010 | Chisolm et al. |
| 2002/0011543 A1 | 1/2002 | Chinn et al. |
| 2004/0011941 A1 | 1/2004 | Roepke et al. |
| 2004/0056159 A1 * | 3/2004 | Schulze ............... 248/125.1 |
| 2005/0006538 A1 | 1/2005 | Turi et al. |
| 2005/0189798 A1 | 9/2005 | Strong |
| 2007/0235623 A1 | 10/2007 | Amisar et al. |
| 2007/0267550 A1 | 11/2007 | Blankenship et al. |
| 2008/0283692 A1 | 11/2008 | Leinen |
| 2009/0142172 A1 | 6/2009 | Blankenship et al. |
| 2009/0294604 A1 | 12/2009 | Sunderland |
| 2009/0314906 A1 | 12/2009 | Cote |
| 2014/0361129 A1 * | 12/2014 | Gomez ............... 248/146 |

FOREIGN PATENT DOCUMENTS

| | | |
|---|---|---|
| CA | 1163893 A | 3/1984 |
| CA | 2549229 A1 | 6/2005 |
| CA | 2685542 A1 | 6/2008 |
| CN | 2481335 Y | 3/2002 |
| CN | 201223591 Y | 4/2009 |
| GB | 2428383 A | 1/2007 |
| WO | 2007100781 A2 | 9/2007 |
| WO | 2008085698 A2 | 7/2008 |
| WO | 2010042091 A1 | 4/2010 |

* cited by examiner

CARRIER FOR PATIENT FLUIDS

FIELD OF THE INVENTION

This invention relates to the field of medical devices, and in particular, to medical devices for delivering medication to patients.

BACKGROUND OF THE INVENTION

One of the most common methods of delivering medications to a patient (usually in a hospital setting, but sometimes elsewhere) is using an intravenous (IV) method in which a needle is inserted into either a peripheral vein (usually the arm) or a central vein (e.g. superior or inferior vena cava). The use of peripheral veins is much more common. Typically, the medication to be delivered is contained in a bag. The nurse or other caregiver hangs the bag on a support unit, typical referred to as an IV pole. The typical prior art IV pole consists of a base support having a 5-star shape, i.e. five bars extending outward radially from a centre, with a caster at the end of each bar. An example of this configuration is shown in U.S. Pat. No. 5,188,323 to David. The bars are typically evenly angularly distributed about 360 degrees A vertical shaft is typically attached at the centre of the 5-star frame, and extends upward, terminating approximately six-and-a-half to seven feet (between 198 centimeters and 214 centimeters) above the floor. At or near the top of the shaft, the prior art IV pole has one or more hangers extending horizontally to hold bags of medication.

In some cases, the bag of medication is simply connected via a drip mechanism and tube to a needle that has been inserted into the vein of the patient, and the rate of medication delivery is dictated by gravity. However, in recent years, it has become more common to use infusion pumps to precisely control the delivery rate of the medication, and the total amount delivered. In the prior art configuration, the pump is clamped to the shaft that extends upwards from the 5-star base. The pump, which is sometimes fairly heavy, is connected to the medication bag and is set in a manner that allows it to control the rate of infusion and the total amount of medication delivered.

In the prior art configuration, the hangers for receiving bags of medication are positioned high off the ground. The reason for this is that, with the bags hanging down, it is desirable not to create any obstructions, where people may, while walking past the IV pole, bump into the bags. Also, because the infusion of medication into the patient relies partly on gravity, placing the bag high off the floor is beneficial because doing so creates more gravitational potential energy.

However, this configuration creates a problem. Specifically, it is hard for many people of average or below-average height to reach the hangers in order to hang bags of medication on the IV pole, or remove hanging bags from the IV pole. In particular, most caregivers who hang IV bags are women, and as compared to men, these women are shorter on average. For women who, for example, are between 150 and 163 cm in height, reaching the hangers to hang medication bags on them can be nearly impossible without standing on a chair or some other piece of furniture.

Even when the hangers for the medication bags are not out of reach, the caregivers, almost inevitably, need to lift the medication bags over their heads. The bags of medication can weigh as much as 4.5-7 kg (10-15 lbs), and a caregiver may need to load such bags on IV poles up to 30-50 times per shift. As a result, caregivers are prone to soreness, strain and injury to arms, neck and shoulders.

Another common problem with the prior art IV pole is that it can be quite difficult to attach a pump to the pole shaft. The pumps are quite heavy and usually need to be held with two hands, with the result that it is difficult to manipulate both the IV pole and the pump to allow the pump to be clamped to the shaft.

Another problem with the prior art IV pole is that it is unstable and susceptible to tipping, particularly, but not solely, as a result of incidental contact between the IV pole and other objects.

Yet another problem that has been found to exist with the prior art IV pole is that it often presents a tripping hazard. Specifically, it is common for patients who require constant connection to an IV pole to walk around pushing the IV pole with one hand. However, it has been found that patients too often inadvertently strike their feet against the X-shaped support base of the prior art IV pole while walking, thus creating a tripping hazard.

SUMMARY OF THE INVENTION

What is desired is a support unit for intravenous medication and medication delivery devices that solves one or more of the above-noted problems, or improves the performance of the IV pole in relation to one or more of the problems described above.

Therefore, according to one aspect of the invention, there is provided a carrier for carrying patient fluids, the carrier comprising:
  a carrying frame;
  a support base, the support base and carrying frame being sized, shaped and mutually positioned such that the carrying frame extends from the support base so as to be supported above the floor by the support base;
  at least one container holder, attached to the carrying frame distal from the floor, the container holder being configured to receive a container of medication, the container holder being movable between an upward position and a downward position;
  at least one holder activator spaced from the container holder and positioned between the container holder and the floor, the holder activator being coupled to the container holder and configured such that the container holder moves toward a downward position in response to a first movement of the holder activator, and toward an upward position in response to a second movement of the holder activator, wherein the first movement and second movement each comprise a pivoting movement.

According to another aspect of the invention, there is provided a carrier for carrying medication to be delivered intravenously to a patient, the carrier comprising:
  a carrying frame;
  a support base, the support base and carrying frame being sized, shaped and mutually positioned such that the carrying frame extends from the support base so as to be supported above the floor by the support base;
  at least one location configured for attachment of a medication delivery device to the carrying frame;
  a container holder, attached to the carrying frame, for holding a container of medication;
  at least one ledge, positioned adjacent to the at least one location, for supporting a medication delivery device, the ledge being positioned between the container holder and the support base;

whereby a medication delivery device may be rested on the ledge while being attached to the carrying frame.

According to another aspect of the invention, there is provided a carrier for carrying medication to be delivered intravenously to a patient, the carrier comprising:

a support base configured to be positioned on a floor, the support base having at least one wheel to facilitate movement of the support base along the floor;

a carrying frame extending from the support base so as to be supported above the floor by the support base;

a container holder, attached to the carrying frame, for holding a container of medication;

a brake, mounted on the support base, for inhibiting movement of the carrier, the brake including a braking element, the brake being sized shaped and positioned such that the braking element pushes against the floor when the brake is engaged to inhibit movement of the carrier, the brake being selectively engageable and disengageable.

According to another aspect of the invention, there is provided a carrier for carrying medication to be delivered intravenously to a patient, the carrier comprising:

a support base configured to be positioned on a floor;

a pole attached to the support base at an attachment point and extending generally vertically from the support base so as to be supported above the floor by the support base;

a container holder, attached to the carrying frame, for holding a container of medication;

a medication delivery device attachment location at a front of the carrier;

the attachment point being positioned rearward of a centre of mass of the carrier when no medication delivery device is attached to a front of the carrier.

BRIEF DESCRIPTION OF THE DRAWINGS

Reference will now be made, by way of example only, to drawings of the invention, which illustrate the preferred embodiment thereof, and in which.

DETAILED DESCRIPTION OF THE PREFERRED EMBODIMENTS

Figure 1:
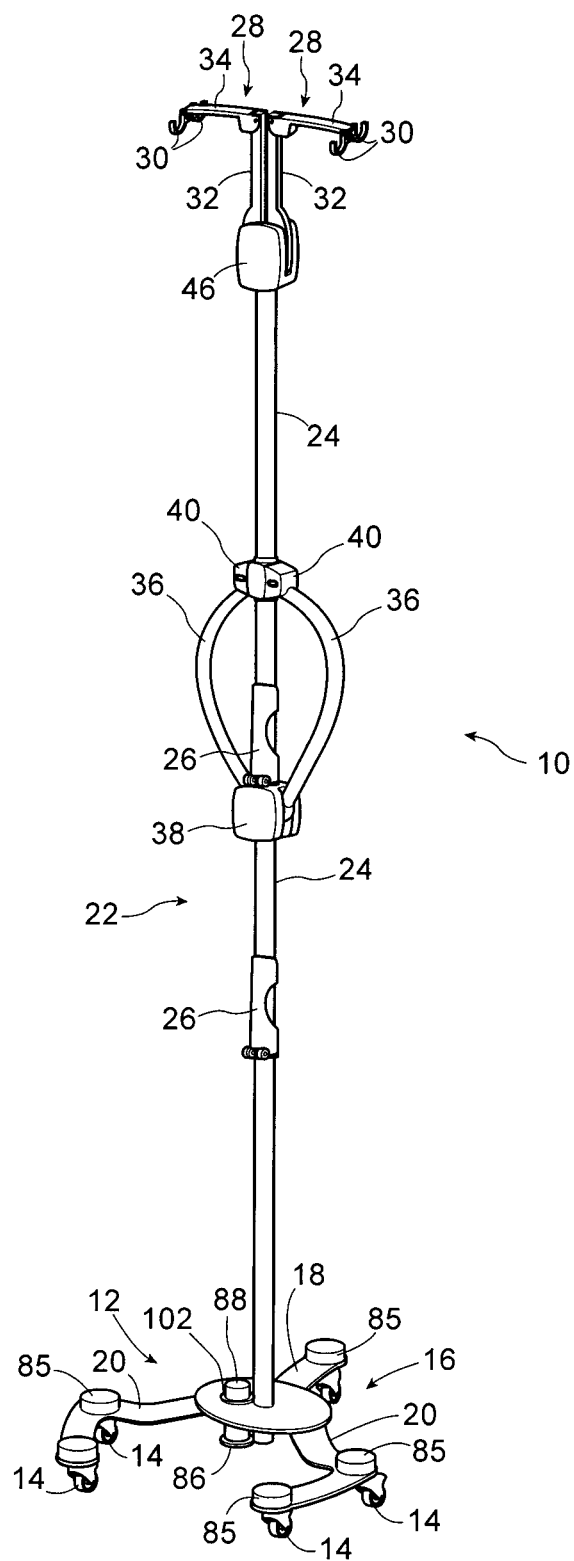
FIG. 1 is a perspective view of an embodiment of the carrier of the present invention.

Referring now to FIG. 1, a carrier 10 for carrying patient fluids is shown. "Patient fluids" refers to medication, non-medication fluids delivered to a patient (e.g. saline solution) and fluid extracted from a patient (e.g. fluid removed by means of a catheter). The IV pole 10 comprises a support base 12 configured to be positioned on a floor (not shown). The preferred support base 12 includes at least one caster or wheel 14 configured to be positioned on a floor, and to facilitate movement by rolling of carrier 10 and base 12 along the floor (the carrier 10 as shown in the drawings includes five wheels). The wheels 14 are preferably mounted to support base frame 16. Support base frame 16 preferably comprises three branches, including a single rearward branch 18 and two forward branches 20 (one right-hand and one left-hand). Preferably, casters 14 are pivotable relative to support base frame 16, facilitating selective changes in the direction of movement of the IV pole 10 along a floor.

The support base 12 preferably supports above the floor a carrying frame 22 that extends from the support base 12. Most preferably, the carrying frame comprises a pole 24 extending generally vertically upward from the support base 12 when the support base 12 is resting on a floor.

Figure 6:
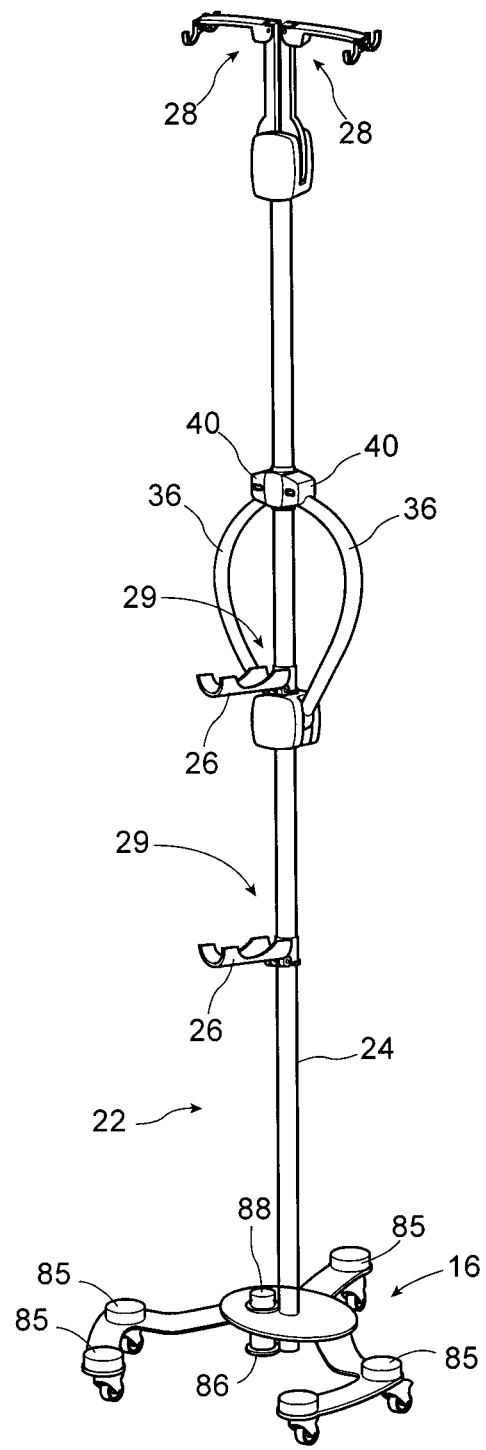
FIG. 6 is a perspective view of an embodiment of the carrier of the present invention.
Figure 7:
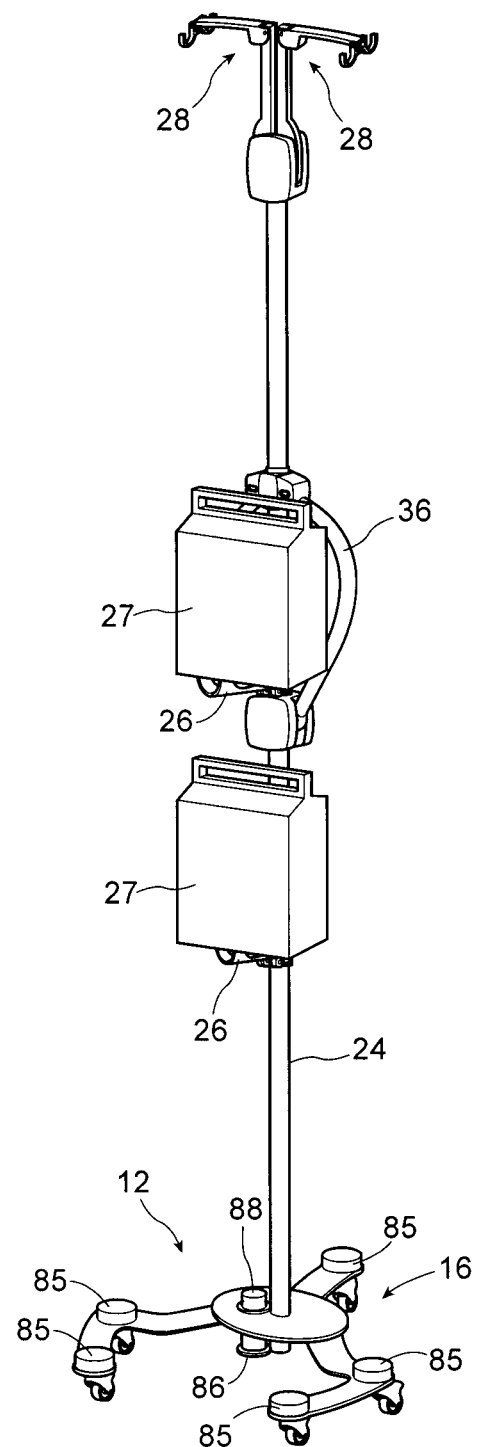
FIG. 7 is a perspective view of an embodiment of the carrier of the present invention, with medication delivery devices.

Mounted to and positioned on the pole 24 are one or more ledges 26. Preferably, the IV pole includes two or three or four or more ledges 26. The optimum number of ledges will vary, depending on the type of patient, hospital ward or caregiving environment the pole 24 is being used in. The preferred ledge 26 has a retracted position (shown in FIG. 1), in which the ledge is positioned generally vertically up against the pole 24. The ledges 26 preferably may also be selectively moved from the retracted position to an extended position, in which they are extending generally horizontally from the pole 24, so that medication delivery devices can rest on the ledges in their extended position. FIG. 6 shows ledges 26 in their extended positions. FIG. 7 shows the ledges 26 in their extended positions, with pumps 27 mounted to pole 24 and resting on ledges 26. Thus, most preferably, the ledges are mounted to pole 24, permitting movement from the retracted position to the extended position, and from the extended position to the retracted position, by pivoting of the ledge 26 relative to pole 24.

The IV pole further includes at least one container holder attached to the pole 24 distal from the support base 12, the container holder being configured to receive and hold container of medication. The container holder preferably takes the form of a hanger 28. It will be appreciated that the invention comprehends other forms of container holders besides hooks and hangers. For example, and without limitation, the invention comprehends as a container holder a shelf or platform, or any other element or group of elements where a medication container can be rested, hooked, gripped, or otherwise positioned. Similarly, although medication for use with this invention is usually found in bags, the invention is not limited to use with medication bags. Rather, the invention may be used with any type of medication container. Furthermore, the term "medication" in not limited to medicines, but for the purposes of this document includes any substance to be delivered intravenously to a patient.

In the preferred embodiment, there are at least two hangers 28, each of which includes one, two, or more than two hooks 30, each hook 30 being configured to receive a container of medication (typically a bag) for hanging from the hook 30. In the preferred embodiment, the hanger is attached to the carrying frame 22 and pole 24 distal from the support base 12. The preferred hanger 28 includes the hanger base portion 32, and a hook carrying portion 34, with the base portion 32 and hook carrying portion 34 being pivotally attached to one another. The base portion 32 is pivotally attached to pole 24.

Figure 2A:
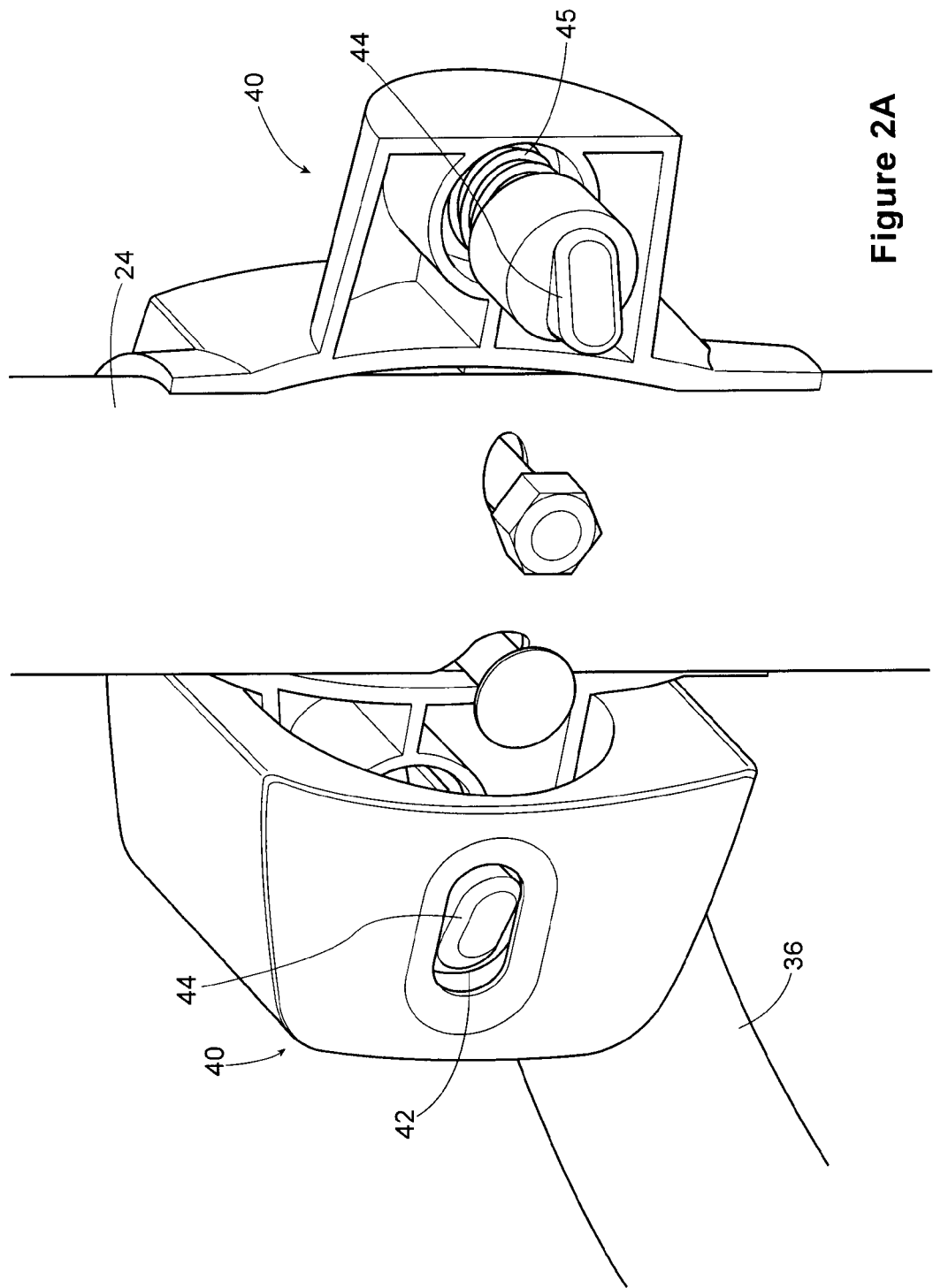
FIGS. 2A and 2B show details of a lock forming part of the preferred embodiment of the present invention.
Figure 2B:
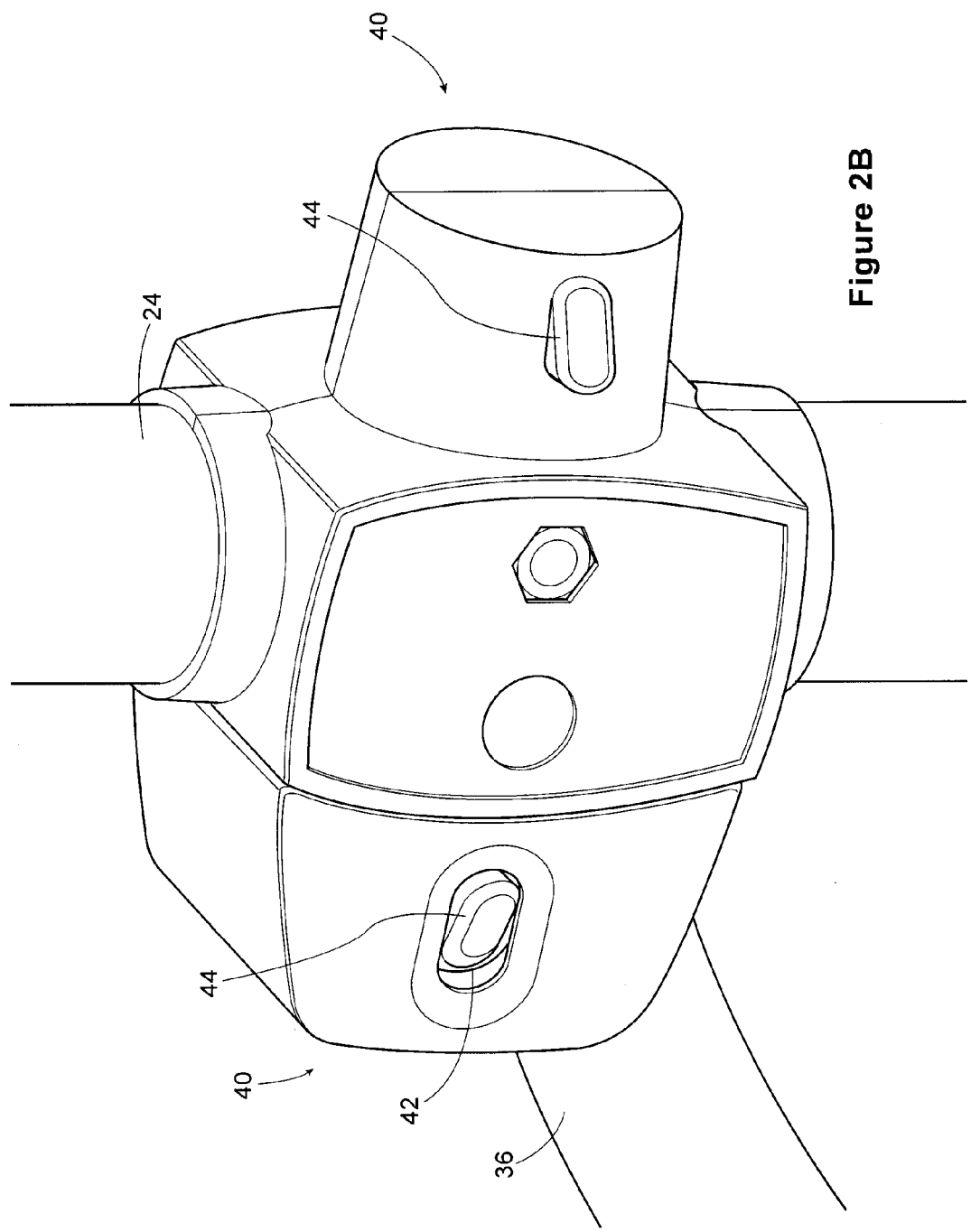
Figure 3:
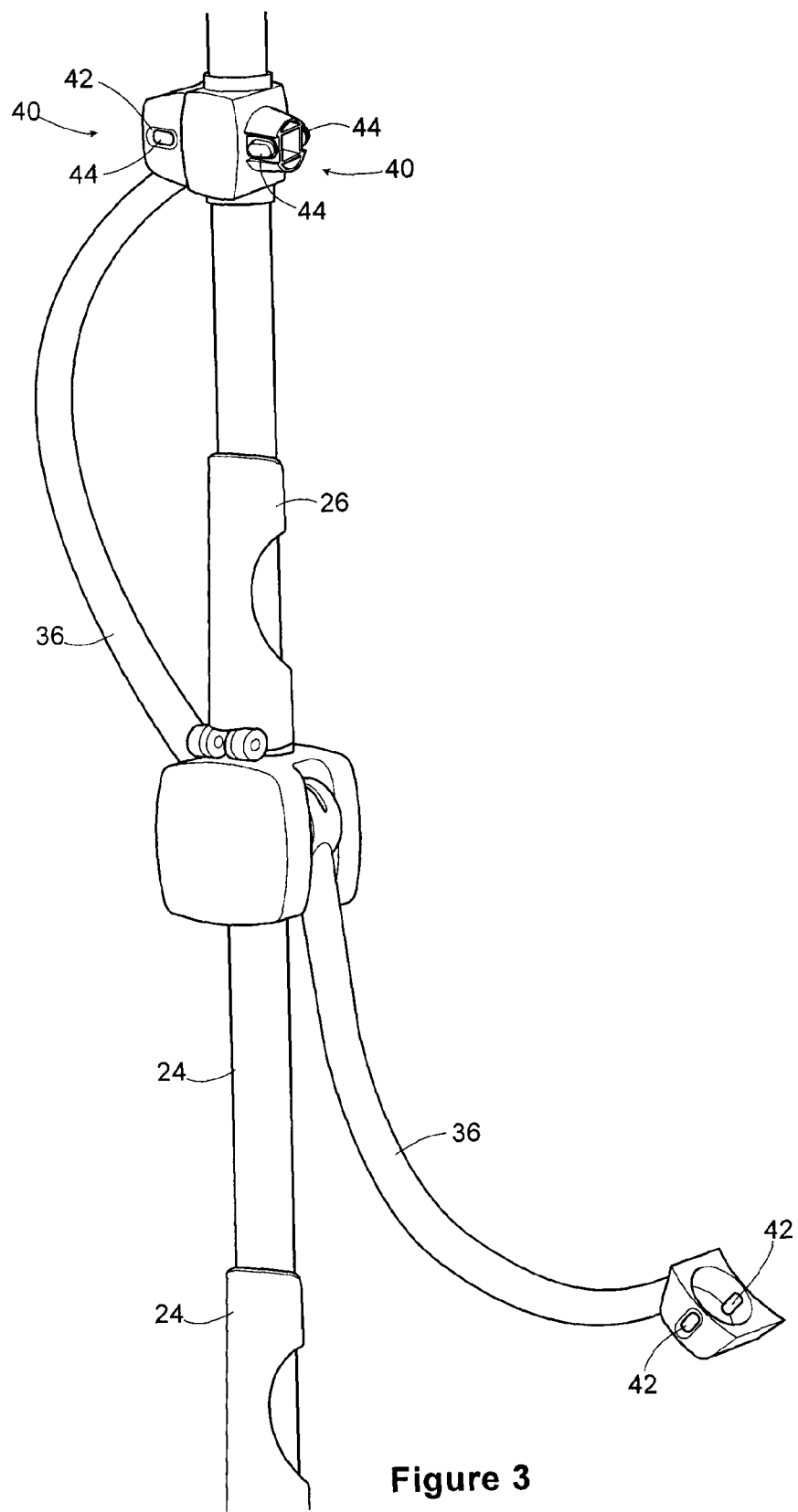
FIG. 3 shows a portion of the carrier of the present invention, including holder activators.

The unit 10 further comprises one or more holder activators, preferably in the form of handles 36 pivotally mounted to pole 24. The handles 36 function to activate the hangers 28 as described below. Handles 36 are preferably lockable to pole 24 at their top ends by means of locks 40, while being pivotally mounted to pole 24 at their bottom ends at joint 38. As shown in FIGS. 2A and 2B, preferably, each handle 36 includes at its top end two locking holes 42 (configured for thumb and forefinger), which are sized, shaped and positioned to mate with locking elements 44. Locking elements 44 are flexibly mounted/coupled to pole 24 on springs 45. When handle 36 is moved from an unlocked or downward position to a locked or upward position, movement of handle 36 causes locking elements 44 flex away from locking holes 42 by compressing spring 45 until the locked position is reached, at which point locking elements 42 spring back to their original position to mate with holes 42 to lock handles 36 in place. In the locked position, elements 44 preferably protrude through holes 42 so that handle 36 is prevented from moving. To unlock handle 36 and move it from the locked or upward position to the unlocked or downward position, the elements 44 can be pushed back to compress spring 45 so that element 44 no longer protrudes through the holes 42, and the handle 36 opened. It will be appreciated that the lock may take a different form and still be comprehended by the invention. For example, each handle may include only one thumb hole for unlocking the handle. Other forms of lock are also comprehended. Furthermore, though not preferred, the handles may have no locks.

A problem with prior art IV poles is that the medication bag hooks are positioned too high. Often, the caregivers cannot comfortably reach the hooks to attach or remove medication bags. Even when the hooks are within reach, the caregiver typically has to reach well over her head to place a heavy bag (often 4.5-7 kg) on the hook, causing strain and sometimes injury, to neck, shoulders and arms. On the other hand, there are benefits to such a configuration, namely, (1) that the bags are out of the way and less likely to be an obstacle to movement by caregivers, and (2) that the high position of the bags creates greater gravitational potential energy to facilitate the movement of the medication into the patient, or into an infusion pump. One aspect of the present invention preserves the advantages of the medication bags being high off of the floor, while mitigating the disadvantages.

Figure 4:
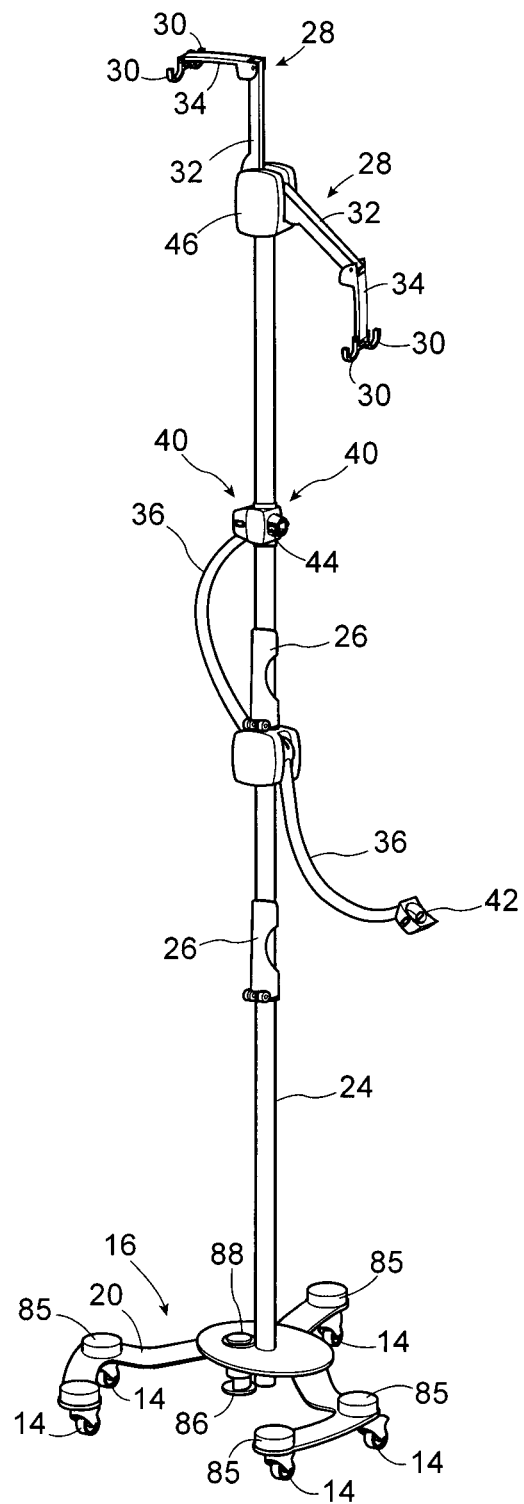
FIG. 4 is a perspective view of an embodiment of the carrier of the present invention.

Handles 36 preferably are spaced from hangers 28, are positioned between hangers 28 and base 16, and function as activators, i.e., activators that function to activate the hangers 28. In the preferred embodiment, both hangers 28 and handles 36 are pivotally mounted to pole 24. In an aspect of the present invention, the hangers 28 have a downward position to which they are moved to permit the easy hanging of one or more medication containers on hooks 30. FIG. 4 shows unit 10 with one of the hangers 28 in a downward position, and another of the hangers 28 in the upward position.

When the hanger 28 is in the downward position, a medication container can more easily be attached to hooks 30 because they are lower in that position than they are in the upward position. Thus, once a caregiver or other user has hung a medication container from hook 30 when hanger 32 is in the downward position, hanger 32 can be moved to its upward position, where it would support the medication container until it is desired to remove the medication container from the unit 10.

The result of this preferred configuration is that the advantages of having the medication container in a high position are preserved, while the disadvantage is mitigated. During use (i.e. while medication from the medication container is being delivered to the patient), the medication container is high off the floor, preferably out of the way, does not create an obstruction for caregivers, and provides sufficient gravitational potential energy for the medication to be delivered efficiently to the patient. Preferably, during use, when the hanger 28 is in its upward position, the hook 30 is about six-and-a-half to seven feet above the floor.

However, when the hanger 28 is in its downward position, the position where the medication bag is hung on or removed from hook 30, hook 30 is positioned lower—preferably less than 6 feet above the floor, and most preferably between five and five-and-a-half feet above the floor.

The handle 36, which functions as a hanger activator, is positioned so as to be easily reachable by the user. Preferably, the top of the handle 36 is about fifty-two inches (plus or minus about six inches) above the floor. It will be appreciated that, with this preferred configuration, a user can activate the hanger 28 to its upward and downward positions by moving the easily reachable handle 36.

To facilitate the movement of the hanger 28 (which is positioned high off the floor) by handle 36 (which is easily reachable), handle 36 is preferably coupled to hanger 28. Generally, hanger 28 may be coupled to handle 36 in any manner that permits a first movement of handle 36 to cause the hanger 28 to move toward its downward position, and a second movement of the handle 36 to cause the hanger 28 to move to its upward position. Preferably, the first movement is a downward movement of handle 36, and the second movement is an upward movement of handle 36, as illustrated by FIG. 4 and FIG. 1. Such a configuration is preferable because it is most intuitive for a typical user—a downward motion moves the hanger 28 down, and an upward motion moves the hanger 28 up. However, it will be appreciated that the first and second movements need not be downward and upward movements respectively. Rather they could be other kinds of movements, such as right and left, or insertion into pole 24 and withdrawal therefrom, or even two consecutive movements in the same direction. There are also other possibilities. What is important is that the hanger activator be coupled to the hanger 28 such that the hanger 28 moves toward the downward position upon a first movement of the hanger activator, and toward the upward position upon a second movement of the hanger activator.

Preferably, the hanger 28 is coupled to the handle 36 by means of an elongate force transmitting coupler. Examples of an elongate force transmitting coupler include, but are not limited to, a rod, cable or the like. In the preferred embodiment illustrated in FIGS. 4, 5 and 11-15, the elongate force transmitting coupler comprises a cable 53 attached to handle 36 and hanger 28. The cable 53 is preferably attached to the handle 36 adjacent the joint 38 at which handle 36 is pivotally attached to pole 24. The cable 53 is preferably attached to hanger 28 adjacent to the joint 46 at which hanger 28 (and in particular, hanger base portion 32) is pivotally attached to pole 24. Cable 53 is preferably attached to hanger 28 by screw 55.

Consider the situation in which the hanger 28 is in its downward position after a first movement of handle 36 to move hanger 28 to the downward position. This is shown in FIG. 4, where both a handle 36 and a hanger 28 are in their downward positions. Most preferably, because of the way the cable 53 is positioned (and in particular, because of how and where it is attached to the handle 36), when the handle 36 is pivoted upward (the second movement), the cable 53 is tightened i.e. tension is increased in the cable 53, and the cable 53 pulls against hanger 28. Because of the position of the cable 53 (and in particular, because of the way it is attached to hanger 28 and base portion 32), when the handle 36 is pivoted upward and the cable 53 tightens, it pulls on the hanger 28 and pivots it toward its upward position. The force imparted by the user to handle 36 is thus transmitted along the length of the cable 53, which functions as a force transmitting elongate coupler. The cable 53 is positioned and configured to that when the handle 36 reaches its upward position and is locked in that position by lock 40, the hanger 38 reaches it upward position, and is held in place against gravity by the tension in the cable 53.

Now consider the situation in which the hanger 28 is in its upward position after a second movement of the handle 36 to cause the hanger to move to the upward position. To move the hanger 28 to its downward position, the handle 36 is pivoted downward (the first movement). The cable 53, which is configured and positioned as described in the previous paragraph, is also configured and positioned so that the downward rotation of the handle 36 loosens the cable 53 i.e. reduces the tension in the cable 53. As the cable 53 loosens and slack is created, the cable 53 no longer tightly holds the hanger 28 in the upward position. Meanwhile, with the loosened cable 53 no longer acting against gravity, gravity will act on the hanger 28 to cause hanger 28 to pivot downward to the downward position. As the handle 36 is rotated further and further downward, more slack is available in the cable 53, and the hanger 28 rotates further and further downward due to gravity until it reaches its downward position. The cable 53 is configured and positioned such that when the handle reaches its downward position (shown in FIG. 4), the hanger 28 also reaches its downward position.

It will be appreciated that other forms of elongate force transmitting couplers are comprehended by the invention. For example, the elongate force transmitting couplers may comprise, for example, a rod or piston or the like, which transmits force along its length between the handle 36 (to which force is applied by a user) and hanger 28 (to which force is transmitted). The invention comprehends thus moving the hanger 28 back and forth between its upward position and its downward position.

It will further be appreciated that the coupling of the hanger 28 and handle 36 need not be done by means of a elongate force transmitting coupler, though such a coupler is preferred. Other modes of coupling are comprehended by the invention. What is important in this aspect of the invention is that the hanger activator be coupled to the hanger 28 such that the hanger 28 moves toward the downward position upon a first movement of the hanger activator, and toward the upward position upon a second movement of the hanger activator.

Referring now to FIGS. 5, 11, 12, 13, 14 and 15 the joint 38 (at which handles 36 are mounted to pole 24) is shown. Adjacent to joint 38, screw 48 attaches the cable 53 to handle 36. The cable 53 extends along channel 50 and then extends upward along a hollow shaft portion 51 of hollow pole 24 toward hanger 28. When handle 36 is rotated downward (in the direction of arrow D), the cable 53 is loosened because the point of attachment of cable 53 (screw 48) rotates so as to be closer than previously to joint 46 and hanger 28. This allows the hanger 28 to move to its downward position by means of gravity acting on hanger 28. When the handle 36 is rotated toward its upward position (in the direction of arrow U), the cable 53 is pulled tight (because screw 48 is rotated away from hanger 28 along the path of the cable 53) and pulls hanger 28 to its upward position.

It will be appreciated that when handle 36 is unlocked and rotated either in an upward or downward direction, the force of gravity will act on the handle 36, and on the hanger 28, and, mainly, on any medication container on hanger 28, thus urging them downward. One possible negative consequence of this fact is that, if the user mistakenly lets go of handle 36 while it is being pivoted, both handle 36 and hanger 28 may fall down to their fully downward positions. Thus, preferably, the device 10 includes a fall preventer, coupled to the handle 36 and hanger 28, that supports handle 36 against the force of gravity, and keeps it from falling if it is released when unlocked.

Figure 5:
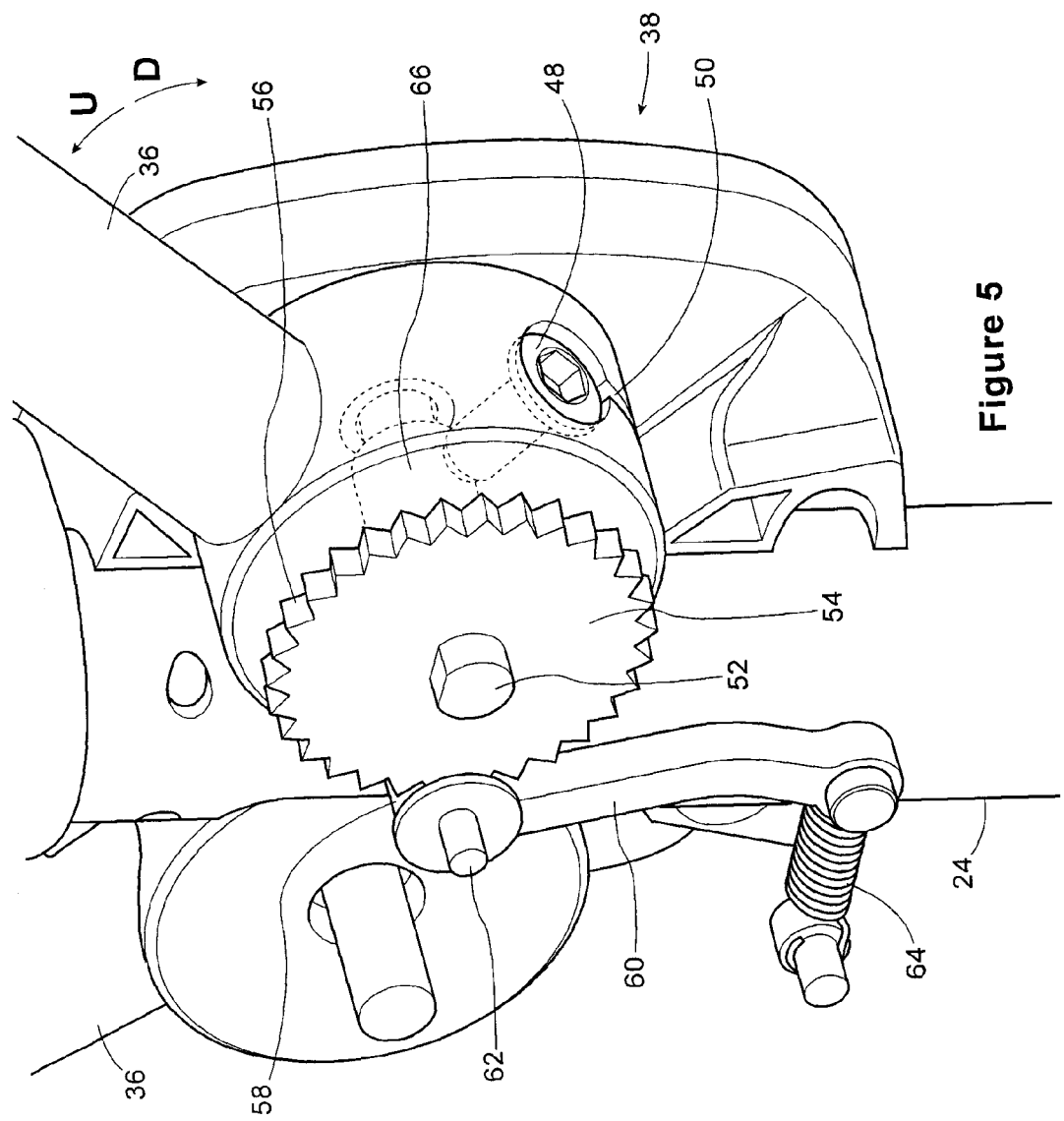
FIG. 5 shows detail of the fall preventer.

In the preferred embodiment shown in FIG. 5, the handle 36 is mounted to the pole 24 by means of an axle 52, mounted to pole 24. Handle 36 is pivotally mounted to axle 52. Operatively coupled to the handle 36 is the fall preventer comprising a ratchet, itself comprising a wheel 54 with teeth 56. The downward position adjuster further comprises a pawl 60 having gripping head 58, pawl 60 being pivotally mounted on shaft 62 to pole 24. Pawl 60 engages with teeth 56. The end of the pawl 60 opposite to head 58 is attached to spring 64, also attached to pole 24.

There is also preferably provided a decoupler, preferably in the form of a one way clutch bearing 66, attached to handle 36, which clutches wheel 54, and causes it to move when handle 36 is rotated in downward direction D, but decouples wheel 54 from handle 36 when it is rotated in upward direction U. The result is that, when handle 36 is rotated in direction D, wheel 54 rotates, but when handle 36 is rotated in direction U, wheel 54 does not rotate.

The head 58 bears on the side of one of the teeth 56, preventing the wheel 54 from rotating in direction D merely because of the force of gravity. However, when handle 36 is pulled by a user in direction D, head 58 slips out from between teeth 56 and wheel 54 turns until spring 64, which biases element 60, causes head 58 to bear against the side of the next tooth. Thus, handle 36 can be rotated by the user in direction D, with the user's applied force overcoming the biasing of spring 64 to cause head 58 to slip from one tooth to the next. Once the applied force stops, the head 58 holds the wheel 54 (and thus the handle 36) in place by bearing against a tooth 56. Head 58 is held in place because it is biased by spring 64 against teeth 56.

Thus, the position of handle 36 is incrementally adjustable once handle 36 is unlocked from lock 40. In other words, handle 36 need not be rotated to its maximally downward position, but can be positioned (without the need of user support) at a downward position located somewhere short of fully downward, and it will remain in place because of element 60 holding wheel 54 in place. Since, preferably, the position of hanger 28 depends on how far down the handle 36 has been rotated, the downward position of hanger 28 is incrementally adjustable, with the increments corresponding to the width of teeth 56.

In the preferred embodiment, the handles 36 are used not only for raising and lowering the hangers, as described above, but also as grips for a user to push the IV pole. It will be appreciated that patients who require intravenous medication are often capable of walking, but must remain connected to the IV pole. Such patients can typically move about while pushing IV pole 10. Handles 36 provide a convenient point at which the patient can hold the IV pole 10 and push it from place to place. In addition, the handles 36 can be used by the patient as a support, to assist patients who have difficulty walking. In this sense, the carrier 10 can be used in a manner similar to a traditional walker, with handles 36 being the place at which the user grips the carrier 10 for support.

It is common for medication delivery devices (e.g. infusion pumps) to be used with IV poles. These pumps may control the rate of medication delivery to the patient, and/or the total amount of medication delivered to the patient. They are typically mounted to the IV pole, as they need to go wherever the patient goes. It has been found, however, that mounting pumps to IV poles is difficult, particularly for an individual caregiver working alone. The pumps are generally quite heavy, and are typically mounted to the pole by means of a clamp at the back of the pump. A user mounting a pump to a pole needs to hold the pump above the floor and against the pole, while at the same time fastening the clamp to the pole. Because of the pump's weight, it is hard to control, particularly with only one arm (since the other is required to operate the clamp). Furthermore, pressing the pump up against the pole typically causes the pole to roll away from the user. Thus, a user needs to hold the (heavy) pump, hold the pole to keep it still, and operate the clamp. Even if the user had three hands, this would be a difficult task.

Thus, preferably, carrier 10 further comprises at least one ledge 26. Ledge 26 is preferably pivotally mounted to pole 24, and in position between the hanger 28 and base 12. Adjacent to the ledge 26 is preferably a location 29 configured for attachment of a medication delivery device to the pole 24. The invention comprehends two ledges, or three ledges, or four ledges, or any number of ledges greater than four. Preferably, the ledges 26 are configured so as to have an extended position for supporting a medication delivery device, such as, for example, a pump, and a retracted position. The ledge 26 is preferably pivoted between the two positions. In its preferred extended position, the ledge 26 is generally perpendicular to pole 24, and thus, generally horizontal, or parallel to, the floor. This position is best suited to the ledge 26 supporting a pump that is being attached to pole 24. However, it will be appreciated that other extended positions are comprehended by the invention, such as, for example, the ledge 26 being angled between the horizontal and vertical floor.

Preferably, in the retracted position, ledge 26 is positioned generally vertically along the pole 24, so as not to protrude from pole 24. Most preferably, the ledge 26 includes a concave region that is sized and shaped to mate with pole 24. Thus, when the ledge 26 is folded up against pole 24 to its retracted position, the pole 24, which is round, fits into the concave shape of ledge 26, with the result that ledge 26 fits snugly against pole 24 and the protrusion of ledge 26 from pole 24 is minimized when the ledge 26 is retracted.

Figure 8:
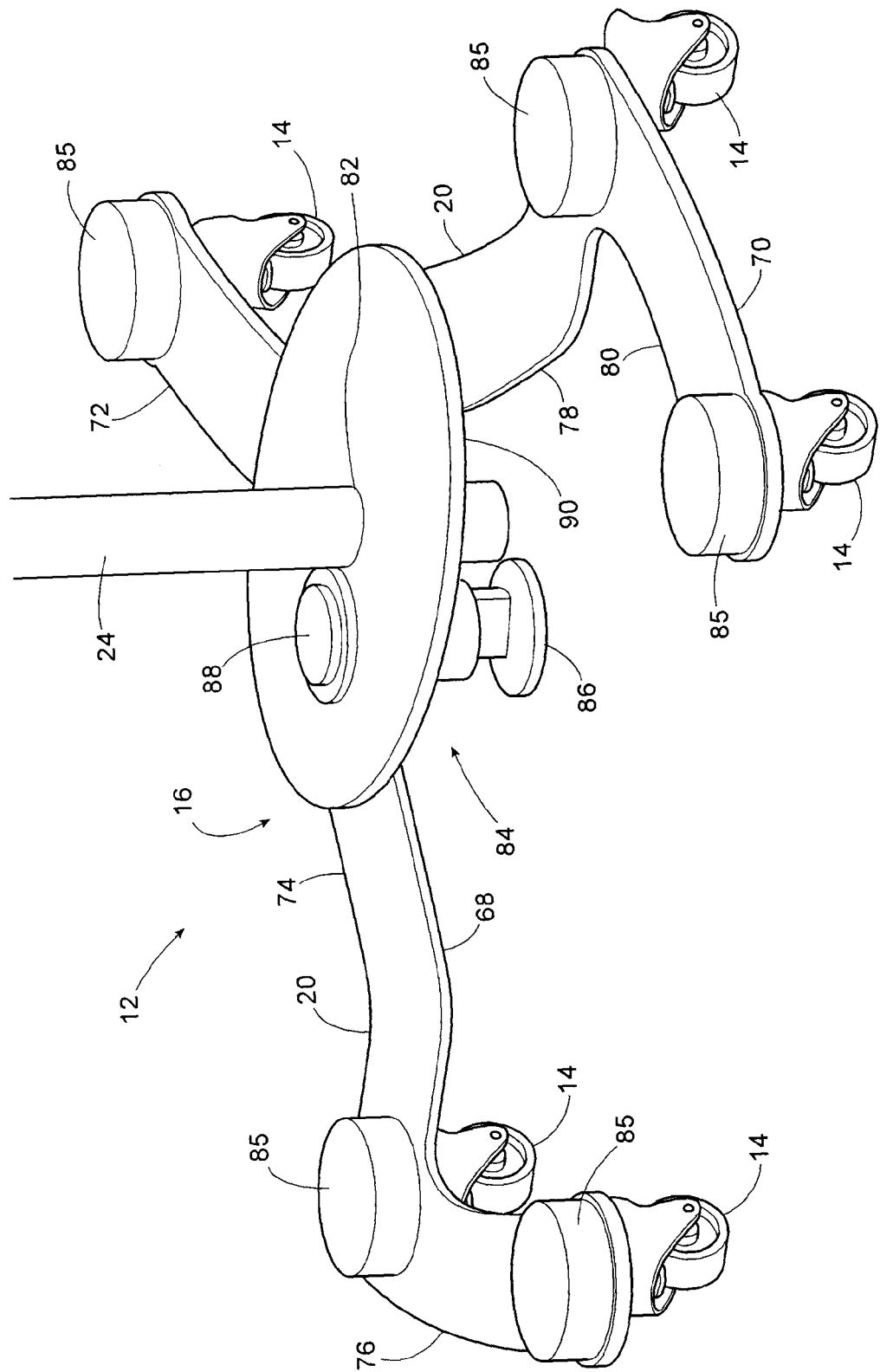
FIG. 8 shows detail of the support base of an embodiment of the present invention.

Referring now to FIG. 8, the preferred support base 12 is shown. The support base comprises support base frame 16. Support base frame 16 comprises three branches, including right-hand forward branch 68 (having two wheels 14 attached thereto), left-hand forward branch 70 (having two wheels 14 attached thereto), and a single rearward branch 72 (having one wheel attached thereto. Rearward branch 72 is preferably substantially straight, and extends substantially in a rearward direction from pole 24. Right-hand forward branch 68 preferably includes a first subbranch 74 that extends forward and rightward from pole 24, and a second subbranch 76 that extends from the end of the first subbranch 74 leftward and forward. Left-hand forward branch 70 includes a third subbranch 78 that extends forward and leftward from pole 24, and a fourth subbranch 80 that extends from the end of the third subbranch 78 rightward and forward. The pole 24 is attached to support base frame 16 at attachment point 82.

It will be appreciated that carrier 10 preferably includes a medication delivery device attachment location 29 at a front of the carrier (see FIG. 6). Thus, in this specification, "front" or "forward" means the side of the pole 24 where the location 29 is, and "rearward" means the other side.

In the prior art 5-star base configuration, the five branches of the base frame are typically symmetrical about the pole 24 and the attachment point 82 of the pole to the base frame. The result is that the centre of mass of the prior art IV pole, when no pump is mounted to it, is positioned approximately directly above the attachment point.

The inventor has discovered that this configuration creates a tipping hazard in the prior art IV pole. Specifically, when a (often heavy) pump is attached to the front of the prior art IV pole, the centre of mass of the combination moves forward from directly above the attachment point to a location forward of the attachment point and of the pole itself. This makes it more likely that the pole, particularly if bumped or knocked, will tip forward and fall, an event that would be dangerous to both patients and caregivers.

The inventor has further discovered that this tipping risk can be reduced by configuring the base, and locating the attachment point, so that the attachment point 82 is positioned rearward of the centre of mass of the carrier 10 when no medication delivery device or pump is attached to a front of the carrier. This way, when the pump is subsequently attached to the front of the pole 24, and the centre of mass of the carrier-pump combination moves forward, the pump will be located on or close to the line of action of the gravitational force through the new centre of mass. By having little or no horizontal displacement between the heavy pump and the centre of mass of the carrier-pump combination, the tipping hazard is reduced substantially, and the combination is more stable.

To the extent a tipping hazard still remains, the carrier is more likely to tip toward the front, since that is where the heavy pump is positioned. In the present invention, this risk is further mitigated by the configuration of the base described above. This includes the configuration of the forward branches, and in particular, the fact that they flair outward and back in toward a point directly in front of pole 24. This part of the base 12 adds weight to the carrier in front of the pump, thus mitigating the tipping hazard. It also provides points of contact between wheels 14 and the floor both to the sides of pole 24 and to the front of pole 24. Finally, because the forward branches are relatively long (especially as compared to the rearward branch), they provide forward points of contact with the floor that are well-displaced forwardly from the pump. The further forward these forward points of contact, the more reduced the forward tipping hazard becomes, since the anti-tipping torque exerted by the floor increases with the distance between these points of contact and the pump.

To further reduce the tipping hazard, the preferred support base frame 16 preferably includes a plurality of stability weights 85 distributed around and spaced from the attachment point 82. The weights 85 preferably number 5 or more, and are preferably distributed surrounding the attachment point 82 and pole 24. It will be appreciated that the weights 85 add stability because the gravitational force on the weights 85 acts as a counter-torque against any pivoting motion that would occur if the carrier 10 were to tip.

Preferably, each weight is made of steel and weighs about one pound, or about 454 grams. It will be appreciated, however, that at least some of the weights will preferably be positioned away from any pivot point about which the carrier would tip. This distance between the weights and pivot point magnifies the anti-tipping counter-torque exerted by the weights 85.

Preferably, the stability weights 85 take the form of discs, having flat tops and bottoms, as shown in FIG. 8. The preferred weights 85 are made of steel. In the preferred embodiment of carrier 10, casters 14 are screwed into holes in the bottoms of weights 85, providing a strong and stable mounting for casters 14.

Figure 9:
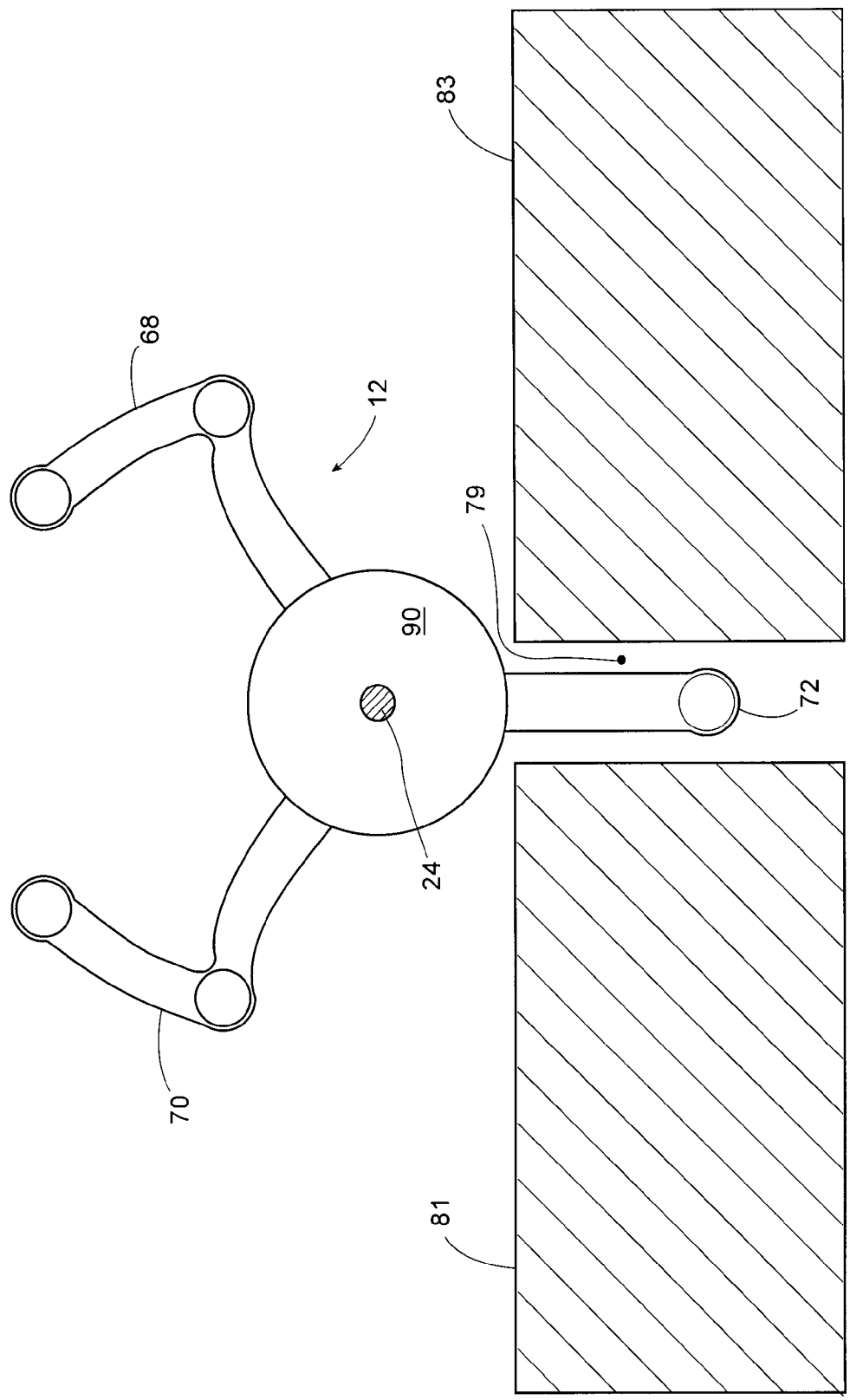
FIG. 9 is a cross-sectional plan view of the support base near objects.

It will also be appreciated that the preferred configuration of base 12 makes the carrier 10 more space efficient. This benefit is illustrated in FIG. 9. FIG. 9 shows two pieces of furniture, 81 and 83, with a small space 79 between them. Having two objects or furniture pieces close together is common in hospital or other patient rooms, and it is also common for such rooms to be small and cluttered, making space efficiency important.

As can be seen, base support 12 is able to fit into space 79 by positioning rearward branch 72 in space 79. This is possible because, in this preferred embodiment, there is only one rearward branch, which is positioned in space 79. If there were other rearward branches (as in the 5-star prior art), they would interfere with inserting one branch of the base into space 79. The result of being able to insert branch 72 into small spaces is that less available floor space is taken up by the carrier 10.

Figure 16:
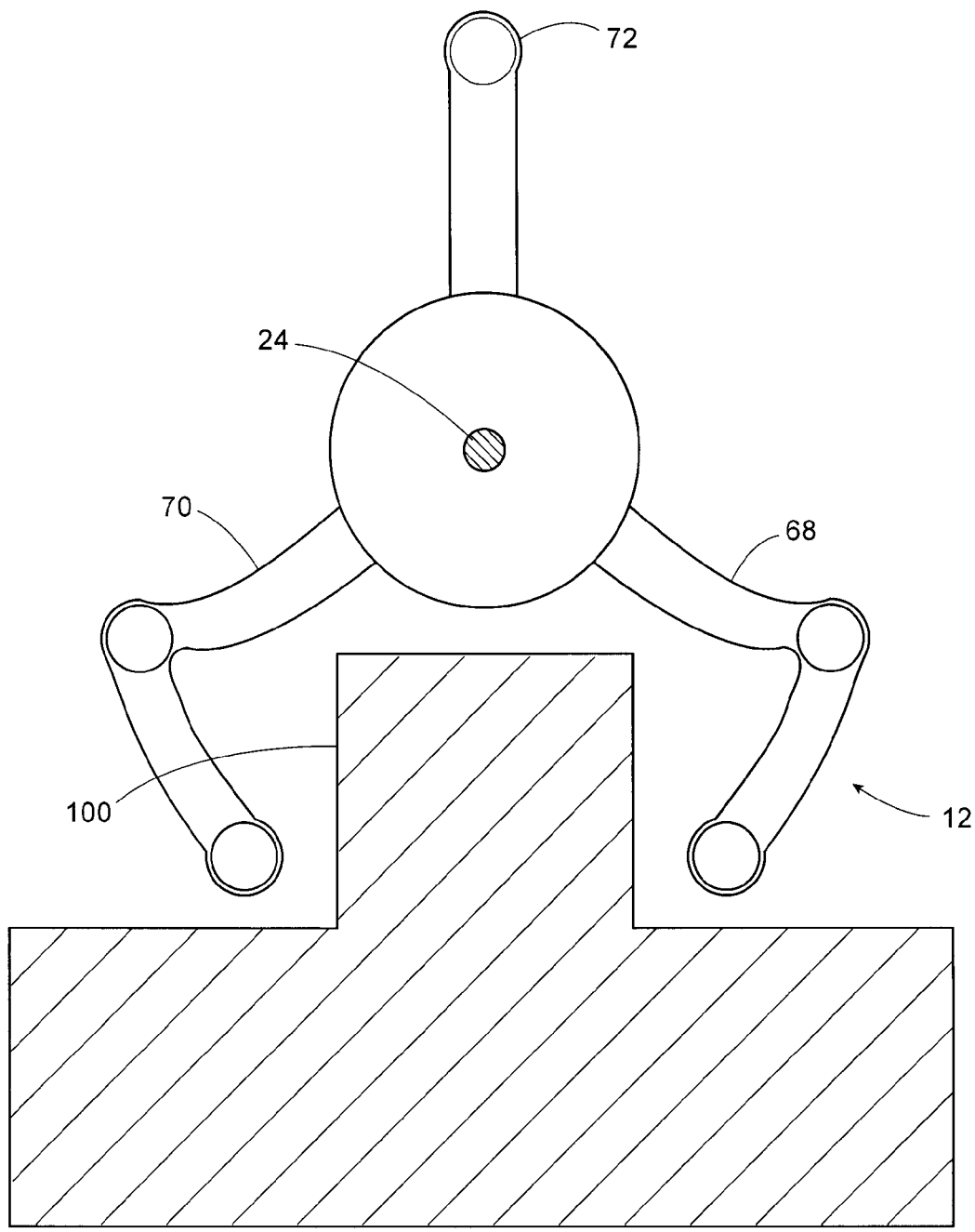
FIG. 16 is a cross-sectional plan view of the support base near objects.

A similar benefit is shown in FIG. 16. That figure shows a protruding object (e.g. a piece of furniture). Because of the configuration of base support 12, and in particular, forward branches 68 and 70. The protruding object 100 fits into the space between forward branches 68 and 70, allowing pole 24 to be positioned immediately adjacent to object 100. The result is a more efficient use of space than would be possible with the prior art 5-star configuration.

Apart from the branch configuration of base support 12, space efficiency benefits are also obtained from the height profile of the preferred base support 12. In prior art devices, the base typically has a tented configuration, in which the base is adjacent to the floor away from the pole, but rises as it approaches the pole. The base of the typical prior art device cannot, therefore, fit easily of fully under a bed or other furniture. By contrast, the preferred support base 12 is horizontal, so that the entire support base 12 is a distance from the floor approximately equivalent to the height of casters 14. As a result, the base support 12 can fit under furniture, beds and the like, and can make use of such spaces, yielding further space efficiency.

It will further be appreciated that the preferred configuration of base 12 reduces the tripping hazard associated with a patient walking with the carrier 10. In the prior art 5-star bases, the branches are splayed, so that a patient pushing the carrier with tend to hit his feet on branches of the base as he walks, and it is very difficult to get the branches out of the way while pushing the carrier. By contrast, because the present configuration has only one rearward branch 72, the patient can walk with the carrier while holding the pole to one side of his body. His feet won't strike the rearward branch 72 as he walks because that branch is to one side of him. His feet won't strike the forward branches because they are too far forward. Thus, the tripping hazard is reduced.

As shown in FIG. 8, the carrier preferably also includes brake 84, mounted to support base frame 16. The preferred brake includes a braking element 86 and pedal 88. The brake is mounted adjacent to pole 24 on support base plate 90, which plate is attached to branches 68, 70 and 72. The brake 84 and plate 90 are sized, shaped and positioned such that the braking element 86 pushes against the floor when the brake is engaged to inhibit movement of carrier 10.

The brake is a foot-operable toggle brake that is actuated by pressing pedal 88. Thus, if the brake 84 is engaged (with element 86 pressing against the floor), then pressing pedal 88 will disengage the brake 84. If the brake 84 is disengaged (with element 86 not pressing against the floor), then pressing pedal 88 will engage the brake 84. The brake 84 is thus selectively engageable and disengageable.

It will be appreciated that since IV poles are typically wheeled for ease of movement, it may sometimes be necessary to brake them. For example, IV poles may drift at bedside, or, as described above, tend to roll when pumps are being attached, or when medication containers are being mounted. Prior art IV poles, if braked at all, typically just have brakes on the casters. However, such brakes are small and hard to operate, and since there are several of them, engaging them and disengaging them is time consuming. By contrast, the present brake 84 is conveniently positioned for easy operation by a user's foot, and only one brake needs to be engaged and disengaged.

Figure 17:
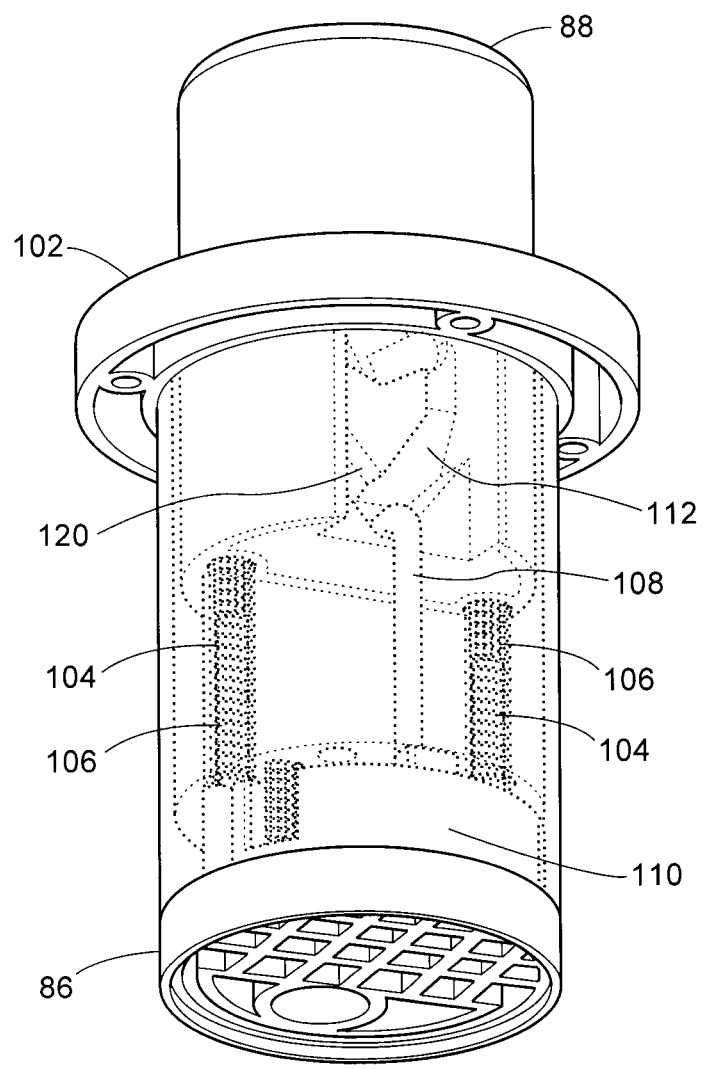
FIGS. 17-20 show detail of the preferred brake.

The brake is shown in greater detail in FIGS. 17, 18, 19 and 20. In FIG. 17, the brake is shown in its disengaged position, with pedal 88 extended, and braking element 86 retracted. Pedal 88 and braking element 86 are mounted to brake housing 102. Pedal springs 106 are positioned on shafts 104, and act between the housing 102 and pedal 88 to urge pedal 88 upward. The brake further includes on-off pin 108, held by on-off pin holder 110, itself attached to housing 102. Additionally, the brake includes channel 112, which contains a shoulder bolt 109 connecting pedal 88 and height adjustment spring 111 mounted between element 86 and pedal 88.

When the brake is disengaged and pedal 88 is depressed, the pin 108 is forced by the shape of first pin channel 112 to move to the right (as shown in FIG. 17) and then curve to the left as the brake reaches its engaged position. In that position, the pin is forced into brake engaged channel 114, shown in FIG. 18. The brake engaged channel 114 is higher up in pedal 88 that the brake disengaged channel 116, and the pin 108 in the brake engaged channel 114 holds the pedal 88 in a retracted position.

Meanwhile, when pedal 88 moves downward, brake element 86 is also extended downward to press against the floor. This pressing against the floor holds carrier 10 in place. The adjustment spring 111 acts between the petal 88 and the element 86 to provide a seating force to seat the element 86 against the floor. It will be appreciated that, in particular circumstances (such as where there is an irregularity in the floor), the standard extension distance element 86 could be too long, or too short. If the distance is too short, the brake won't reach the ground. If it is too long, either the brake will push the carrier 10 up off the floor, creating instability and a tripping hazard, or it will simply not be engageable, because the movement of the pedal 88 and element 86 would be blocked by the floor.

The use of adjustment spring 111 allows the brake to have a long standard extension distance to ensure it always reaches the floor, while substantially lowering the risk of encountering an irregularity in the floor that is severe enough to block the brake from engaging. When the brake is engaged, the element 86 bears against the floor, with the seating force of the spring 111 pushing it against the floor to provide an effective grip. Spring 111, meanwhile, allows the extension distance of the element 86 to adapt to the local height of the floor by adjusting the position of element 86 by means of spring 111.

Figure 18:
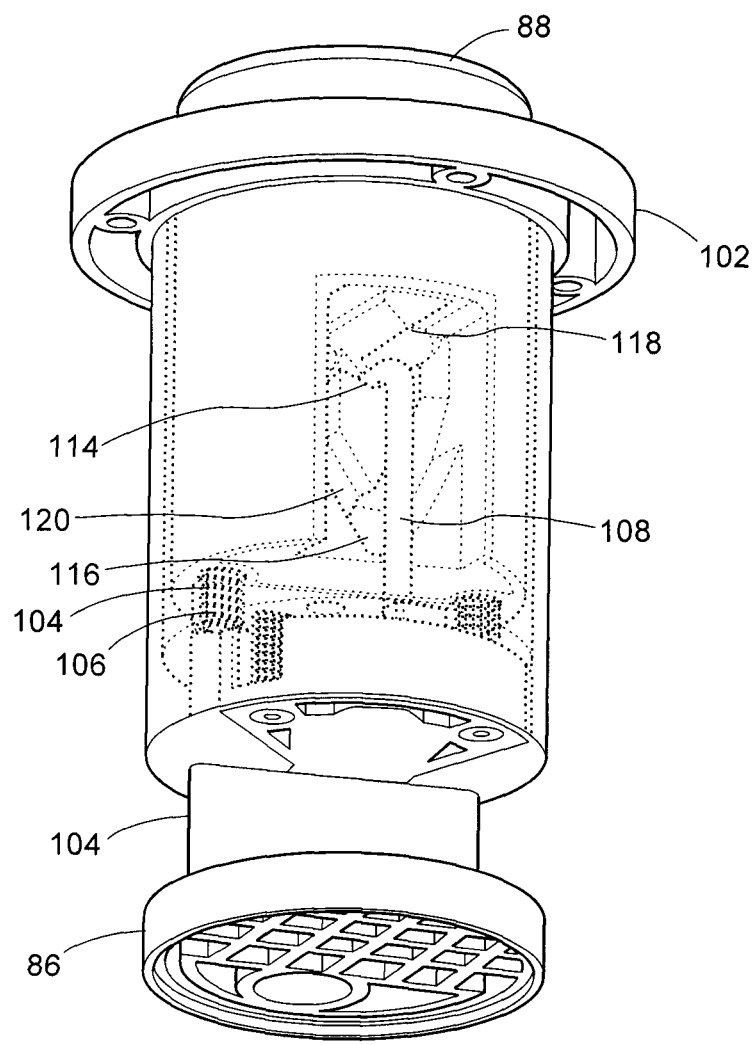
Figure 19:
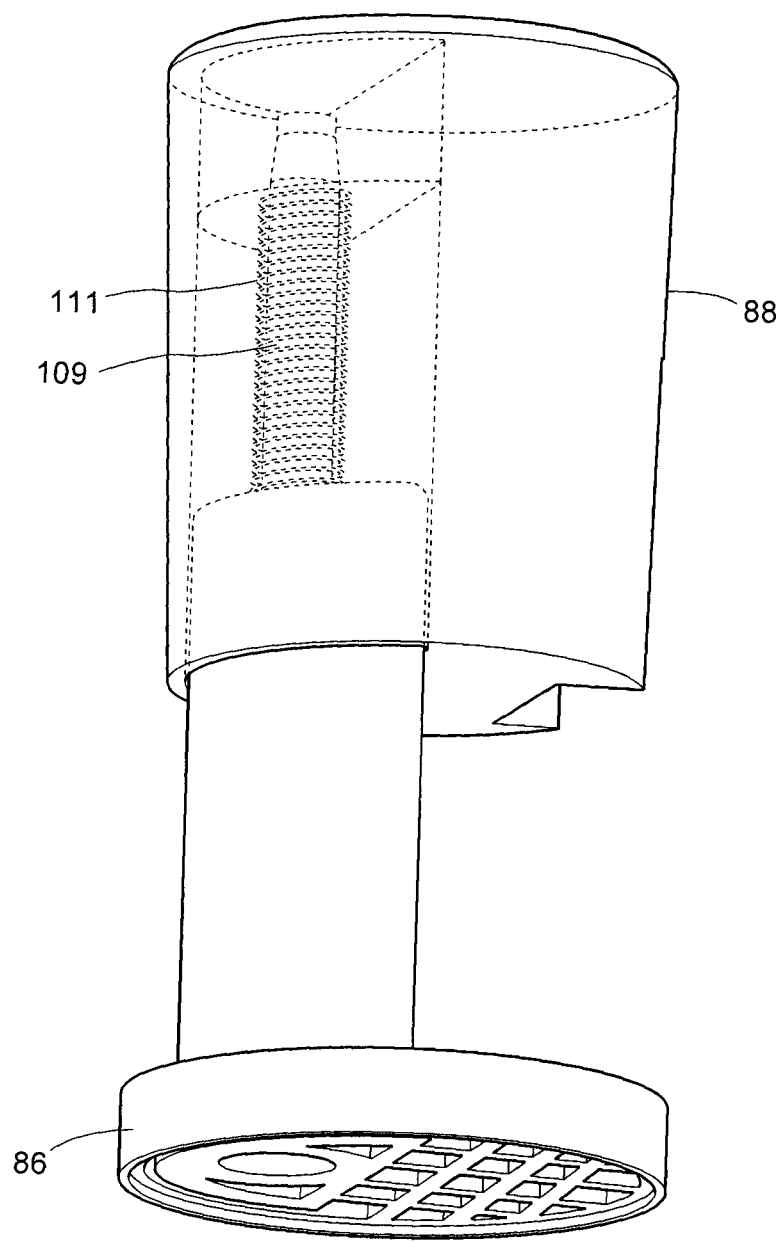
Figure 20:
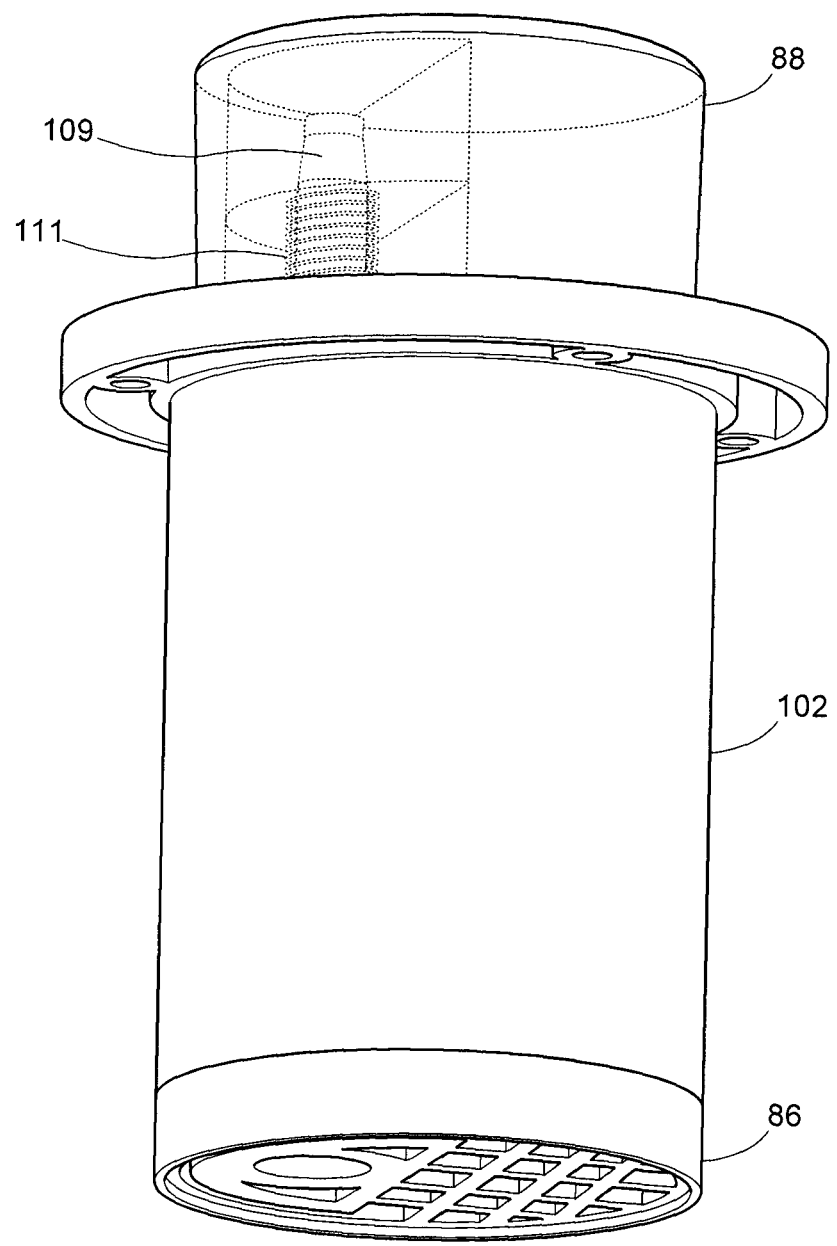

To disengage the brake, pedal 88 is again depressed. Pin guide 118 moves downward, guiding pin 108 to the left (as shown in FIG. 18). Then, as springs 104 drive pedal 88 upward once the pin 108 has moved leftward, pin 108 is guided along second pin channel 120 until it comes to a rest at in brake disengaged channel 116. Thus, the pedal is both engaged and disengaged by depressing pedal 88.

Figure 10:
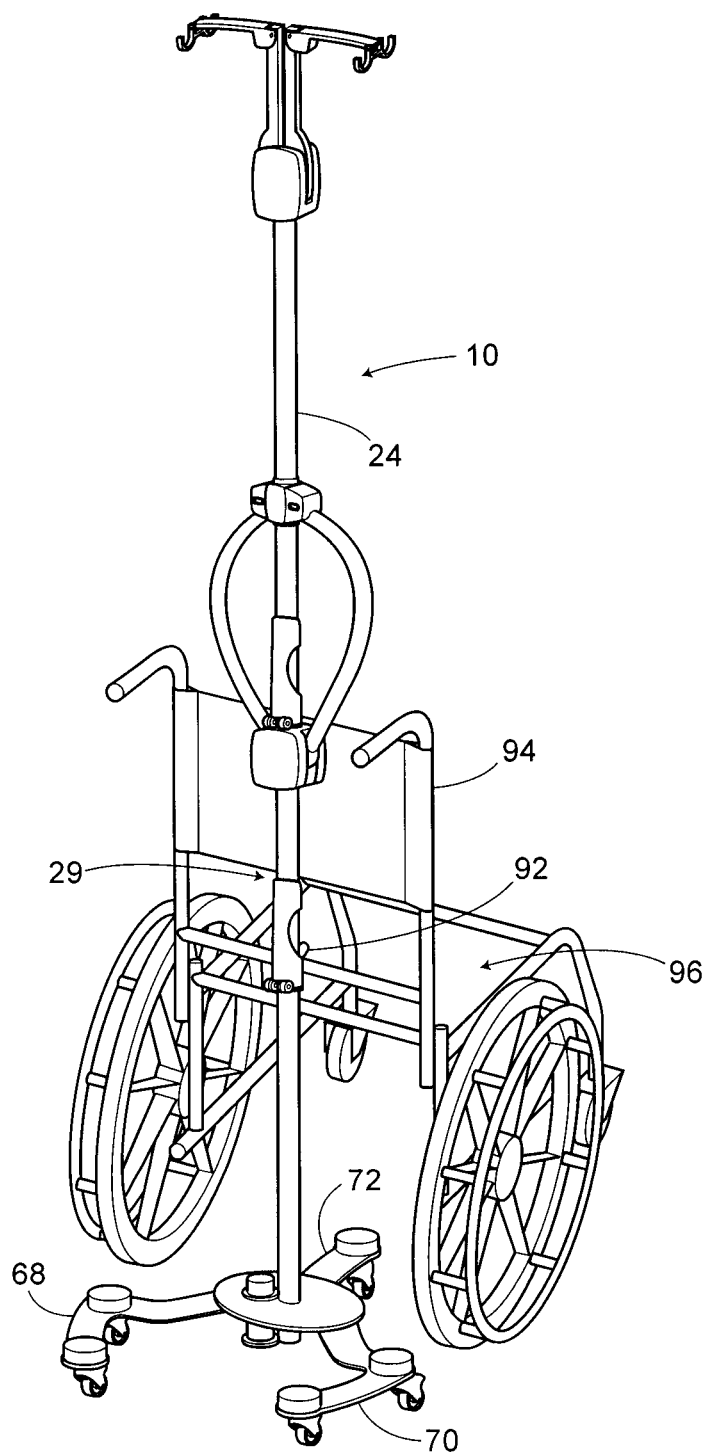
FIG. 10 shows the carrier connected to a wheelchair.
Figure 11:
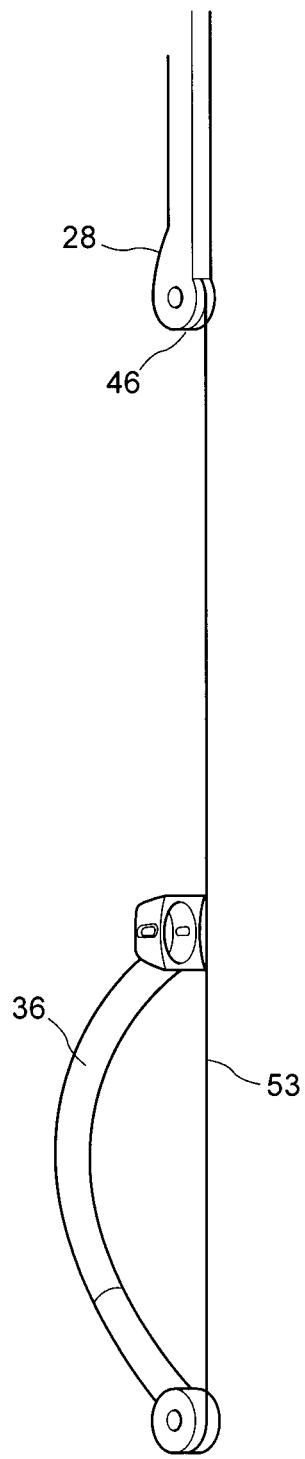
FIG. 11 shows selected detail of the holder activator, container holder and their coupling.
Figure 12:
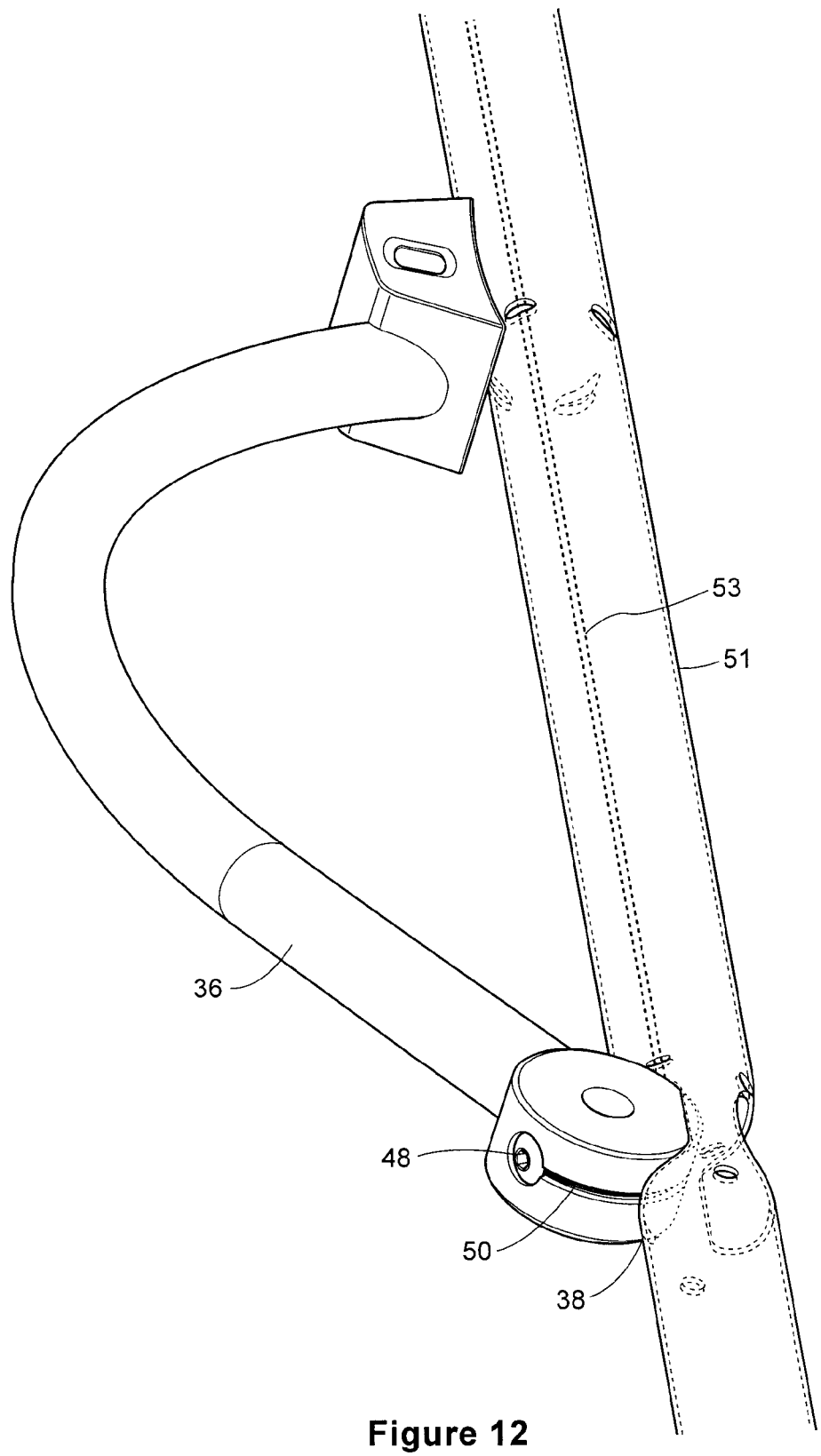
FIG. 12 shows selected detail of the holder activator, container holder and their coupling.
Figure 13:
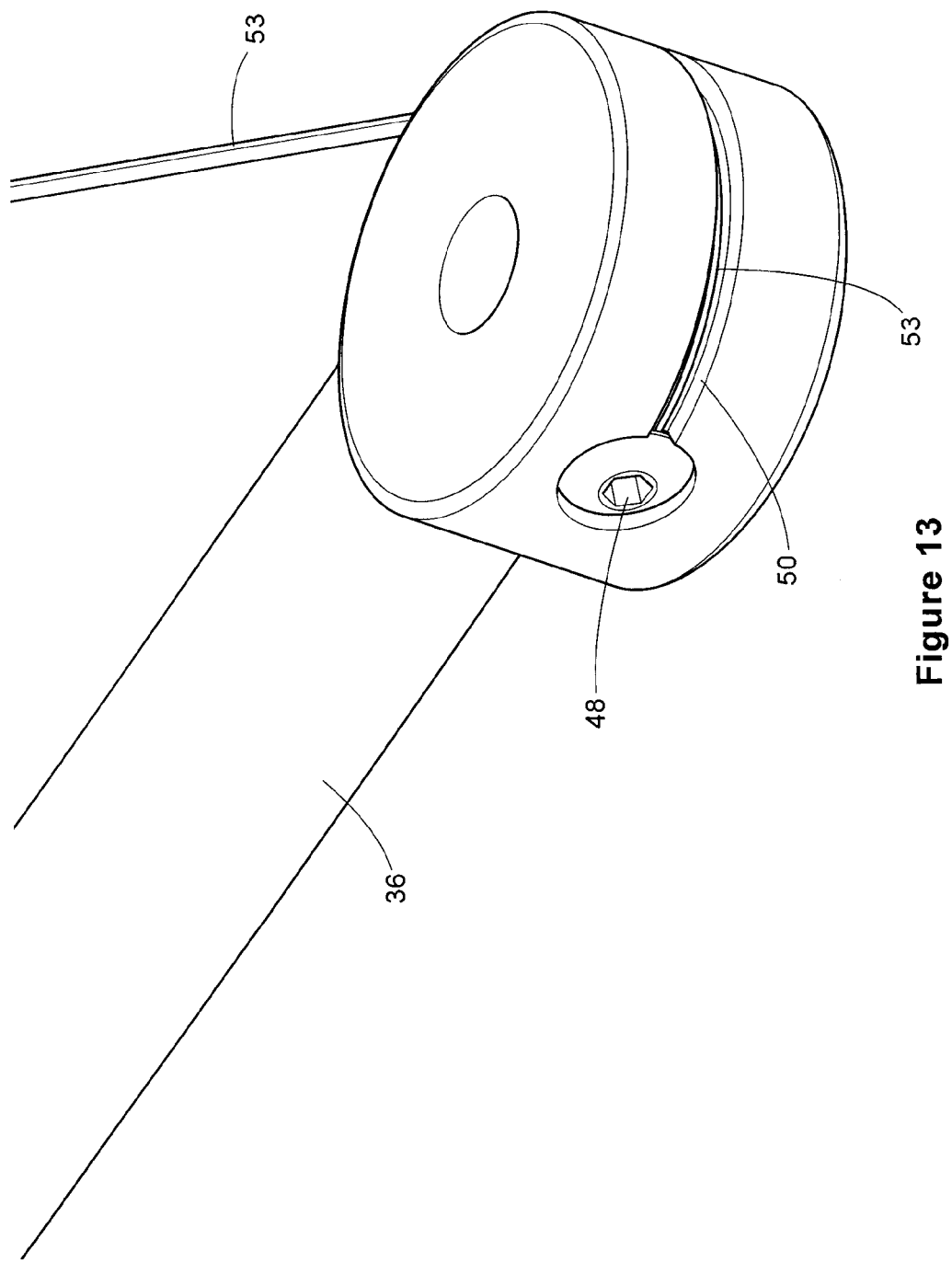
FIG. 13 shows selected detail of the holder activator, container holder and their coupling.
Figure 14:
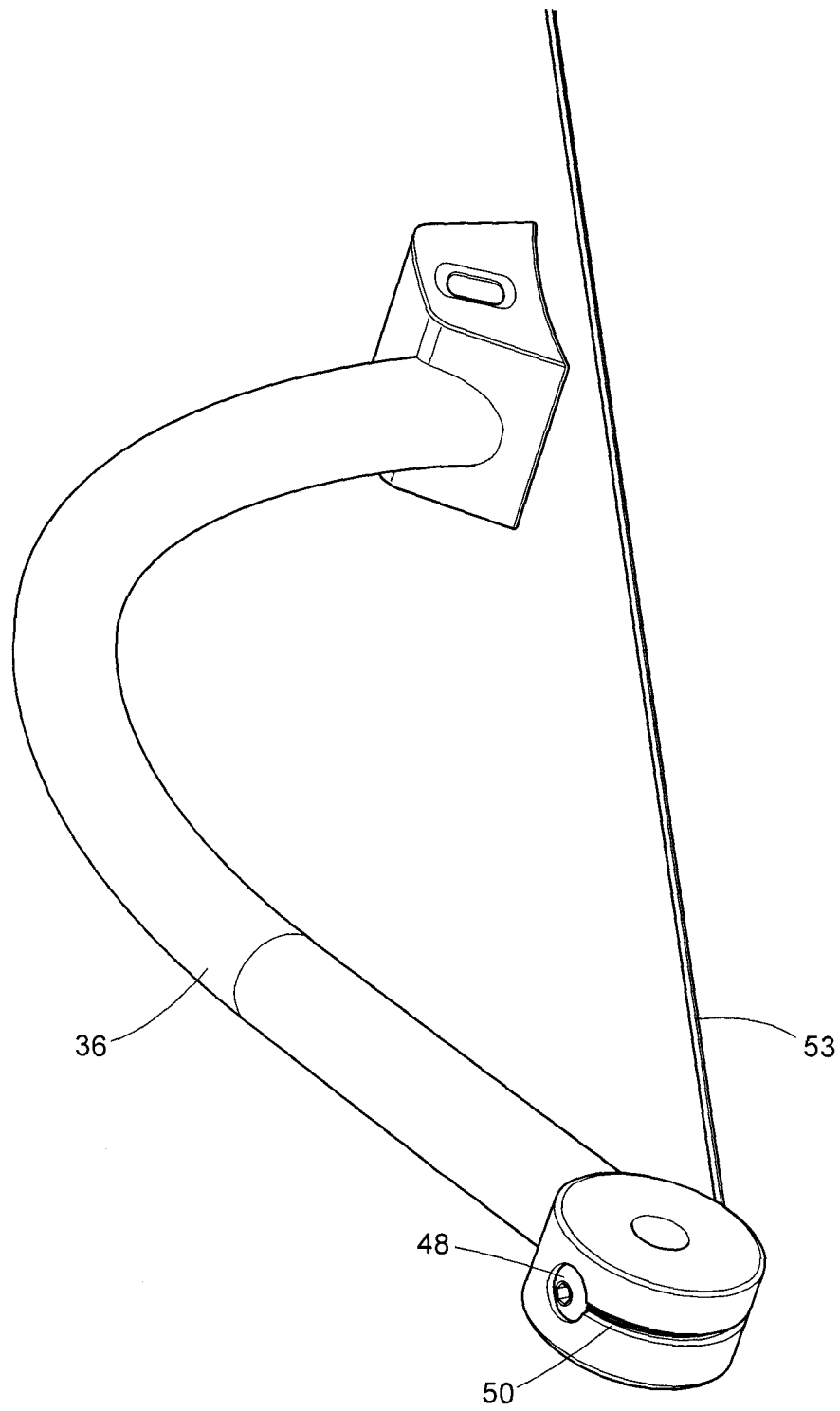
FIG. 14 shows selected detail of the holder activator, container holder and their coupling.
Figure 15:
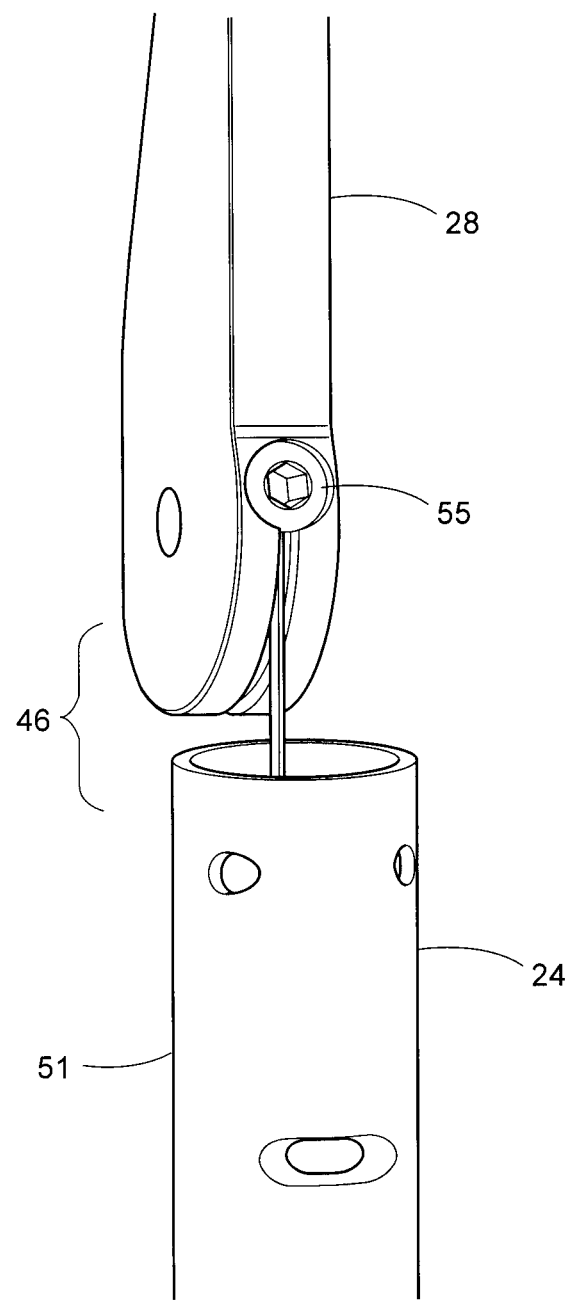
FIG. 15 shows selected detail of the holder activator, container holder and their coupling.

Referring to FIG. 10, the carrier 10 is shown connected to a wheelchair 94 by means of clamp 92 mounted on pole 24. The configuration of base 12 provides an easy and space efficient way to allow a wheelchair-bound user to move with carrier 10 without having to hold carrier 10 in his hand. Specifically, the rearward branch 72 is positioned under seat 96 of chair 94, thus permitting carrier 10 to be held close to wheelchair 94. As chair 94 rolls, it pulls wheeled carrier 10 with it. Location 29 (and thus any pumps attached to pole 24) are positioned on the opposite side of pole 24 from chair 94. Meanwhile, all the wheelchair-using patient needs to do to wheel the carrier 10 is to propel his wheelchair 94.

It will be appreciated that the 5-star prior art configuration could not be used in this manner, as the splayed branches could not fit under seat 96 without interfering with the wheels of the wheelchair 94.

Various modifications and alterations are possible to the form of the invention without departing from the scope of the broad claims attached hereto. For example, brake 84 may take a different form from that described, as may the carrier frame. Also, though the preferred embodiment comprises a support base on a floor supporting the carrier frame, the support base could be positioned elsewhere and still be comprehended by the invention.

The embodiments of the invention in which an exclusive property or privilege is claimed are defined as follows:

1. A carrier for carrying patient fluids, the carrier comprising:
    a support base;
    a carrying frame, wherein the carrying frame extends from the support base so as to be supported above the floor by the support base;
    at least one location configured for attachment of a medication delivery device to the carrying frame;
    at least one container holder, attached to the carrying frame distal from the floor, the container holder being configured to receive a container of medication, the container holder being movable between an upward position and a downward position;
    at least one holder activator spaced from the container holder and positioned between the container holder and the floor, the holder activator being coupled to the container holder and configured such that the container holder moves toward a downward position in response to a first pivoting movement of the holder activator, and toward an upward position in response to a second pivoting movement of the holder activator.

2. A carrier as claimed in claim 1, wherein the container holder comprises a hanger and wherein the container comprises a bag.

3. A carrier as claimed in claim 1, wherein the container holder is pivotally movable between the upward position and the downward position.

4. A carrier as claimed in claim 1, wherein the holder activator is pivotally mounted to the carrying frame, and wherein the first movement comprises pivoting the holder activator in a downward direction, and the second movement comprises pivoting the holder activator in an upward direction.

5. A carrier as claimed in claim 1, wherein carrier comprises an elongate force transmitting coupler coupling the holder activator to the container holder.

6. A carrier as claimed in claim 5, wherein the elongate force transmitting coupler comprises a cable.

7. A carrier as claimed in claim 6, wherein the cable is attached to the holder activator and to the container holder such that (1) the second movement loosens the cable so that the container holder moves toward the downward position by means of gravity, and (2) the first movement tightens the cable and pulls the container holder toward the upward position.

8. A carrier as claimed in claim 6, wherein the carrying frame includes a hollow shaft portion, and wherein the cable extends along the hollow shaft portion.

9. A carrier as claimed as claim 1, wherein the carrier includes a fall preventer coupled to the holder activator to prevent the holder activator from falling if released when unlocked.

10. A carrier as claimed in claim 9, wherein the fall preventer comprises a ratchet and pawl.

11. A carrier as claimed in claim 9, the holder activator further comprising a decoupler to decouple the holder activator from the fall preventer during the second movement of the holder activator.

12. A carrier as claimed in claim 10, the holder activator further comprising a decoupler to decouple the holder activator from the fall preventer during the second movement of the holder activator, the decoupler comprising a one way clutch bearing configured to clutch the ratchet during the first movement but to release the ratchet during the second movement.

13. A carrier as claimed in claim 1, the carrier further comprising a lock to lock the holder activator to the carrying frame so as to hold the container holder in its upward position.

14. A carrier as claimed in claim 1, wherein the support base and the carrying frame are attached at an attachment point, the support base further including a plurality of stability weights, spaced from the attachment point, for preventing the carrier from tipping.

15. A carrier as claimed in claim 14, wherein the support base includes casters, the casters screwed into the stability weights.

* * * * *